United States Patent
Sowden et al.

(10) Patent No.: US 12,275,954 B2
(45) Date of Patent: Apr. 15, 2025

(54) METHOD OF IDENTIFYING L/M-OPSIN AND CRX POSITIVE CONE PHOTORECEPTOR CELLS BASED ON SPECIFIC BIOMARKERS

(71) Applicant: UCL BUSINESS Ltd., London (GB)

(72) Inventors: Jane Sowden, London (GB); Jorn Lakowski, London (GB); Robin Ali, London (GB); Emily Welby, London (GB); Anai Gonzalez Cordero, London (GB)

(73) Assignee: UCL BUSINESS Ltd., London (GB)

( * ) Notice: Subject to any disclaimer, the term of this patent is extended or adjusted under 35 U.S.C. 154(b) by 757 days.

(21) Appl. No.: 16/488,380

(22) PCT Filed: Feb. 21, 2018

(86) PCT No.: PCT/GB2018/050452
§ 371 (c)(1),
(2) Date: Aug. 23, 2019

(87) PCT Pub. No.: WO2018/154295
PCT Pub. Date: Aug. 30, 2018

(65) Prior Publication Data
US 2020/0063095 A1  Feb. 27, 2020

(30) Foreign Application Priority Data
Feb. 24, 2017 (GB) ...................... 1703058

(51) Int. Cl.
*C12N 5/07* (2010.01)
*A61K 9/00* (2006.01)
*A61K 35/30* (2015.01)
*C12N 5/071* (2010.01)
*C12N 5/0735* (2010.01)
*C12N 5/074* (2010.01)
*C12N 5/079* (2010.01)
*C12N 5/0793* (2010.01)
*C12N 5/0797* (2010.01)
*G01N 33/53* (2006.01)
*G01N 33/569* (2006.01)
*G01N 33/68* (2006.01)

(52) U.S. Cl.
CPC ............ *C12N 5/062* (2013.01); *A61K 9/0048* (2013.01); *A61K 35/30* (2013.01); *G01N 33/56966* (2013.01); *G01N 33/68* (2013.01); *C12N 2506/02* (2013.01); *C12N 2506/45* (2013.01)

(58) Field of Classification Search
CPC ............ C12N 5/0621; C12N 5/0623; C12N 2506/02; C12N 5/0647; C12N 5/0606; C12N 5/0663; C12N 5/0696; C12N 5/0607; C12N 5/0667; C12N 5/0662; C12N 5/0664; C12N 5/0678; C12N 5/0692; C12N 5/0697; C12N 5/16; A61K 35/08; A61K 35/545; A61P 27/02; A61P 25/00
See application file for complete search history.

(56) References Cited

U.S. PATENT DOCUMENTS

| | | |
|---|---|---|
| 8,790,637 B2 | 7/2014 | Mistry et al. |
| 8,961,956 B2 * | 2/2015 | Kimbrel .............. C12N 5/0662 424/93.7 |
| 8,962,321 B2 * | 2/2015 | Kimbrel .................. A61P 35/00 435/325 |
| 9,352,003 B1 * | 5/2016 | Semler ............... A61L 27/3847 |
| 9,526,749 B2 * | 12/2016 | Walker ...................... A61P 3/10 |
| 9,994,815 B2 * | 6/2018 | Reichman ............ C12N 5/0621 |
| 10,280,400 B2 * | 5/2019 | Ohlemacher .......... C12N 5/062 |
| 10,307,444 B2 * | 6/2019 | Lanza ..................... A61P 27/06 |
| 10,973,953 B1 * | 4/2021 | Semler .................... A61L 27/38 |
| 11,214,771 B2 * | 1/2022 | Kuwahara ............ A61L 27/383 |
| 11,214,772 B2 * | 1/2022 | Kuwahara ........... A61L 27/3895 |
| 11,241,460 B2 * | 2/2022 | Lanza ..................... C12N 5/062 |
| 2011/0150845 A1 * | 6/2011 | Parekkadan ............ A61P 37/00 506/14 |
| 2012/0177618 A1 * | 7/2012 | Parekkadan ........... A61K 35/28 435/372 |

(Continued)

FOREIGN PATENT DOCUMENTS

CA  2 912 984 A1  11/2014
EP  1 589 097 A1  10/2005

(Continued)

OTHER PUBLICATIONS

Gatta et al., BMC Genomics, 2014; 14:635. www.biomedcentral.com/1471-2164/14/635.*

(Continued)

*Primary Examiner* — Chang-Yu Wang

(74) *Attorney, Agent, or Firm* — Nelson Mullins Riley & Scarborough LLP; Jane E. Remillard, Esq.; Jeanne M. DiGiorgio

(57) ABSTRACT

The present invention relates to the identification of photoreceptors or cone photoreceptors in populations of cells. In particular the present invention relates to methods of identification of photoreceptors or cone photoreceptors and methods of isolating photoreceptors or cone photoreceptors. Photoreceptors or cone photoreceptors isolated by the methods of the present invention are useful for transplantation and the treatment of retinal dystrophies. Also claimed are human cell populations enriched for photoreceptors or cone photoreceptors and kits for identifying photoreceptors or cone photoreceptors.

7 Claims, 14 Drawing Sheets

(56) References Cited

U.S. PATENT DOCUMENTS

| | | | |
|---|---|---|---|
| 2012/0301958 A1 | 11/2012 | Kazanecki et al. | |
| 2013/0058905 A1* | 3/2013 | Slukvin | C12N 5/0647 435/366 |
| 2013/0183272 A1* | 7/2013 | Kimbrel | A61P 19/00 435/325 |
| 2014/0072537 A1* | 3/2014 | Kimbrel | C12N 5/0647 435/325 |
| 2014/0255356 A1* | 9/2014 | Victor | A61K 35/35 435/378 |
| 2014/0294778 A1 | 10/2014 | Lanza et al. | |
| 2015/0050248 A1* | 2/2015 | Kerkis | A61P 9/00 424/93.7 |
| 2015/0157668 A1* | 6/2015 | Walker | C12N 5/0676 435/366 |
| 2015/0272994 A1* | 10/2015 | Kimbrel | C12N 5/0662 424/93.3 |
| 2016/0030480 A1 | 2/2016 | Mistry | |
| 2016/0038543 A1* | 2/2016 | Kimbrel | A61K 35/28 424/93.21 |
| 2016/0060596 A1* | 3/2016 | Reichman | C12N 5/0621 435/366 |
| 2016/0175362 A1* | 6/2016 | Lanza | C12N 5/0623 435/325 |
| 2017/0021058 A1* | 1/2017 | Huang | A61K 27/3645 |
| 2017/0087190 A1* | 3/2017 | Walker | A61P 3/10 |
| 2017/0211039 A1* | 7/2017 | Ohlemacher | C12N 5/062 |
| 2017/0252374 A1* | 9/2017 | Kimbrel | A61P 3/00 |
| 2017/0274048 A1* | 9/2017 | Neves | A61P 21/00 |
| 2017/0313976 A1* | 11/2017 | Kuwahara | C12N 5/062 |
| 2017/0313981 A1* | 11/2017 | Kuwahara | A61L 27/383 |
| 2019/0060370 A1* | 2/2019 | Lanza | A61K 9/0048 |
| 2019/0127690 A1* | 5/2019 | Kuwahara | G01N 33/15 |
| 2019/0134265 A1* | 5/2019 | Semler | A61K 38/19 |
| 2019/0175656 A1* | 6/2019 | Kimbrel | C12N 5/0647 |
| 2019/0351103 A1* | 11/2019 | Mandai | C12N 5/0621 |
| 2020/0009193 A1* | 1/2020 | Han | C12N 5/0663 |
| 2021/0178022 A1* | 6/2021 | Semler | A61L 27/38 |
| 2021/0182552 A1* | 6/2021 | Kimbrel | C12N 5/0647 |

FOREIGN PATENT DOCUMENTS

| | | |
|---|---|---|
| EP | 3029140 A1 | 6/2016 |
| WO | 2005/042730 A2 | 5/2005 |
| WO | 2013/123292 A1 | 8/2013 |
| WO | 2014/174492 A1 | 10/2014 |
| WO | 2015/158855 A1 | 10/2015 |
| WO | 2016/090215 A2 | 6/2016 |
| WO | 2016/099949 A2 | 6/2016 |

OTHER PUBLICATIONS

Zhou et al., J. Cell Sci. 2015; 129:2169-2178 doi:10.1242/jcs. 169086.*

Kaewkhaw et al., Stem Cells, 2015; 33:3504-3518.*

Eberle et al., "Subretinal transplantation of MACS purified photoreceptor precursor cells into the adult mouse retina," Journal of Visualized Experiments, vol. 84, e50932 (2014).

Eberle, D., et al., "Increased integration of transplanted CD73-positive photoreceptor precursors into adult mouse retina," Investigative ophthalmology & Visual Science, vol. 52(9):6462-6471(2011).

Eberle, D., et al., "Outer segment formation of transplanted photoreceptor precursor cells," PloS one, vol. 7(9):e46305 (2012).

Fei, Y. & Hughes, T. E., "Transgenic expression of the jellyfish green fluorescent protein in the cone photoreceptors of the mouse," Vis Neurosci,, vol. 18: 615-23 (2001).

Gonzalez-Cordero, A. et al., "Recapitulation of human retinal development from human pluripotent stem cells generates transplantable populations of cone photoreceptors," Stem Cell Reports, vol. 9(3): 820-837 (2017).

Komaromy, A. M. et al., "Targeting gene expression to cones with human cone opsin promoters in recombinant AAV," Gene Ther, vol. 15: 1049-1055 (2008).

Koso, H. et al., "CD73, a novel cell surface antigen that characterizes retinal photoreceptor precursor cells," Investigative Ophthalmology & Visual Science, vol. 50(11): 5411-5418 (2009).

Akowski, J., et al., "Effective transplantation of photoreceptor precursor cells selected via cell surface antigen expression," Stem Cells, vol. 29(9):1391-1404 (2011).

Akowski, J., et al., "Isolation of human photoreceptor precursors via a cell surface marker panel from stem cell- derived retinal organoids and fetal retinae," Stem Cells, vol. 36(5):709-722 (2018).

Akowski, J., et al., "Transplantation of Photoreceptor Precursors Isolated via a Cell Surface Biomarker Panel From Embryonic Stem Cell-Derived Self-Forming Retina," Stem Cells, vol. 33: 2469-82 (2015).

Li, Q., et al., "Cone-specific expression using a human red opsin promoter in recombinant AAV," Vision Res, vol. 48: 332-338 (2008).

Mertens, J., et al., "Evaluating cell reprogramming, differentiation and conversion technologies in neuroscience," Nature Reviews Neuroscience, vol. 17: 424-437 (2016).

Meyer, J. S., et al., "Modeling early retinal development with human embryonic and induced pluripotent stem cells," Proc Natl Acad Sci U S A, vol. 106: 16698-703 (2009).

Nathans, J., et al., "Molecular genetics of human blue cone monochromacy," Science, vol. 245: 831-838 (1989).

Wang, Y. et al., "A locus control region adjacent to the human red and green visual pigment genes," Neuron, vol. 9, 429-440 (1992).

* cited by examiner

Fig. 2A

| CD marker | 12wk pR2.1.GFP retinal explant | | 17wk pR2.1.GFP retinal explant | |
|---|---|---|---|---|
| | % of pR2.1.GFP+ and CD marker + cells | % of pR2.1.GFP- and CD marker + cells | % of pR2.1.GFP+ and CD marker + cells | % of pR2.1.GFP- and CD marker + cells |
| CD57 | 100 | 90.3 | 100 | 72.9 |
| CD47 | 100 | 98.2 | 100 | 97.4 |
| CD59 | 91.1 | 94.8 | 96.3 | 97.7 |
| CD200 | 58.9 | 33.6 | 90.9 | 70.2 |
| CD151 | 85.6 | 86.6 | 81.1 | 91.7 |
| CD63 | 6.11 | 10.2 | 78 | 52.2 |
| CD98 | 55.6 | 56 | 75 | 95.7 |
| CD26 | 7.3 | 0.095 | 73.3 | 4.64 |
| CD147 | 23.3 | 4.56 | 68.9 | 32.3 |
| CD120a | 13.3 | 0.26 | 68.3 | 6.29 |
| CD81 | 5 | 2.49 | 64 | 13.9 |
| CD49c | 5.7 | 2.96 | 58.5 | 30.9 |
| CD90 | 34.4 | 5.97 | 54.3 | 31 |
| CD165 | 3.8 | 1.86 | 51.8 | 23.1 |

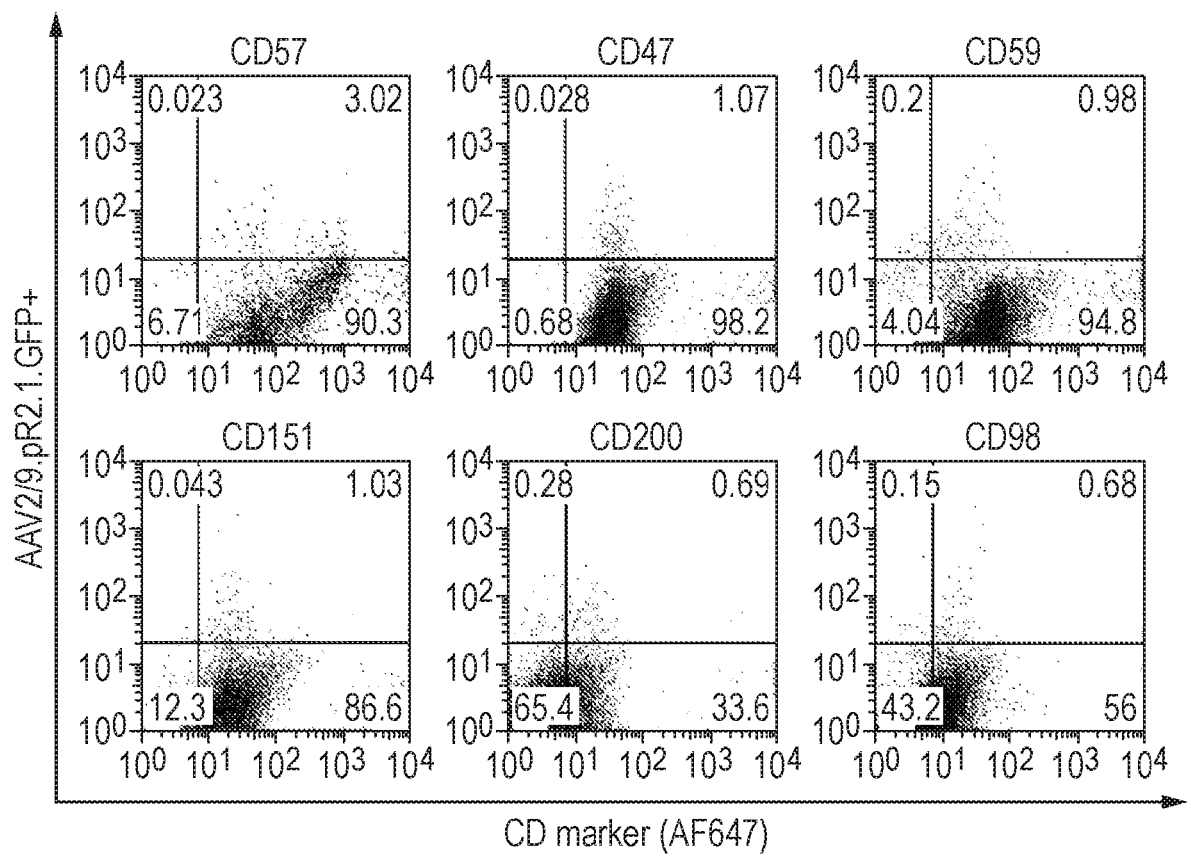

13wk pR2.1.GFP retinal explant

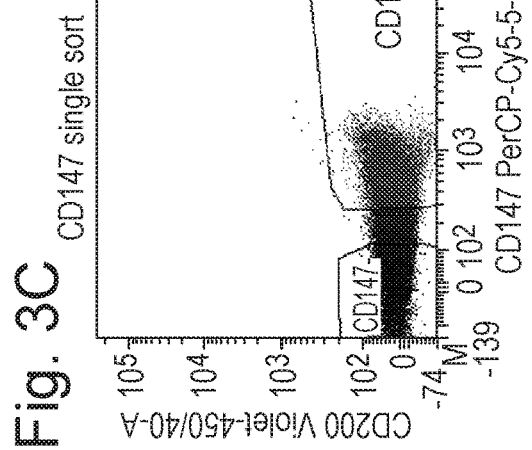
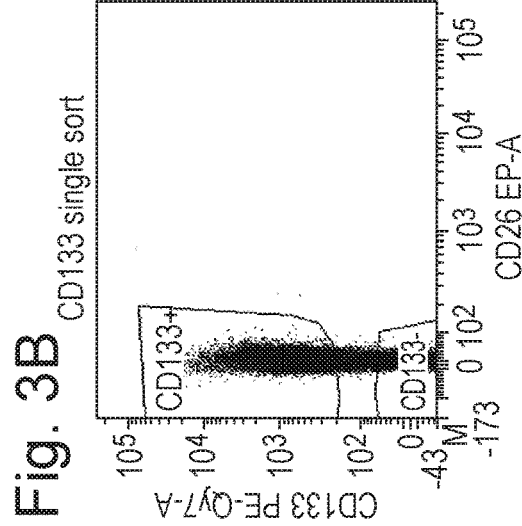
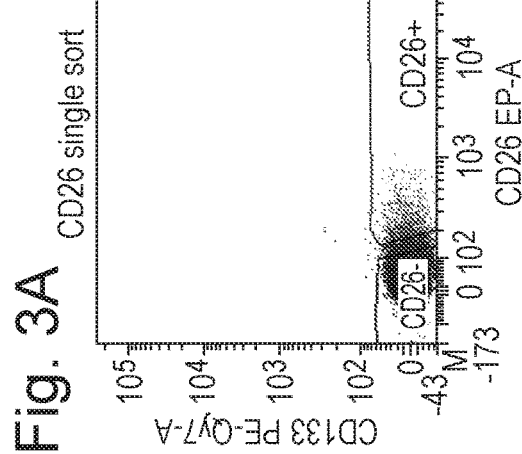
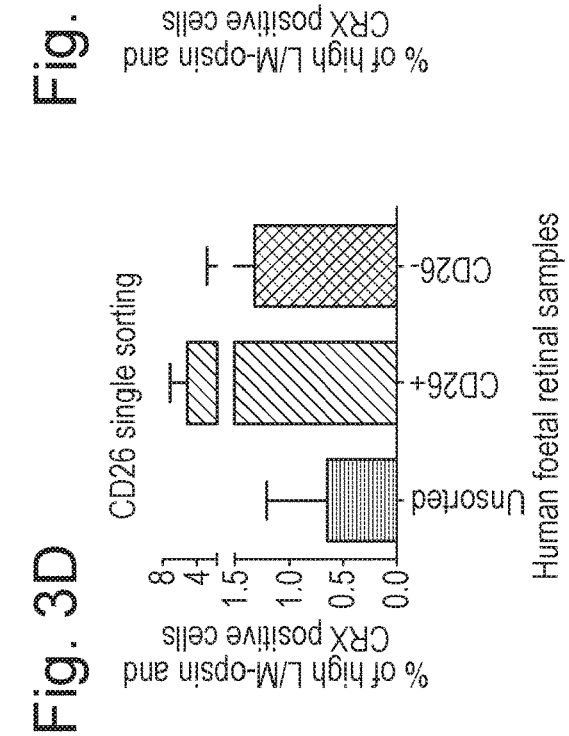

L/M-opsin/Crx

L/M-opsin/Crx

L/M-opsin/Crx

METHOD OF IDENTIFYING L/M-OPSIN AND CRX POSITIVE CONE PHOTORECEPTOR CELLS BASED ON SPECIFIC BIOMARKERS

CROSS-REFERENCE TO RELATED APPLICATIONS

This application is a 35 U.S.C. 371 national stage filing of International Application No. PCT/GB2018/050452, filed Feb. 21, 2018, which claims priority to United Kingdom Application No. 1703058.6, filed Feb. 24, 2017. The entire contents of these applications are incorporated herein by reference in their entirety.

FIELD OF THE INVENTION

The present invention relates to the identification of photoreceptors or cone photoreceptors in populations of cells. In particular the present invention relates to methods of identification of photoreceptors or cone photoreceptors and methods of isolating photoreceptors or cone photoreceptors. Photoreceptors or cone photoreceptors isolated by the methods of the present invention are useful for transplantation and the treatment of retinal dystrophies. Also claimed are human cell populations enriched for photoreceptors or cone photoreceptors and kits for identifying photoreceptors or cone photoreceptors.

BACKGROUND OF THE INVENTION

Rod and cone photoreceptors, which are located in the outer nuclear layer within the retina, are the primary sensory cells of the mammalian visual system. Stimulation by light results in the initiation of the visual transduction cascade, whose information is relayed to bipolar cells, processed by horizontal and amacrine interneurons, and eventually sent by retinal ganglion cells to the visual processing centres in the brain. As the mammalian nervous system has limited regenerative capacity, any disease or injury to retinal photoreceptors leads inevitably to visual impairment or even blindness. In industrialized countries, degenerative conditions affecting photoreceptors, such as retinitis pigmentosa (RP), age-related macular degeneration (AMD), or Leber's congenital amaurosis, are one of the main causes of blindness.

However, current therapies can at best slow down the disease progression but not cure the condition or reverse its effects. This is mainly due to the fact that the details of retinal histogenesis, maintenance and pathology are not sufficiently well understood, for the development of effective therapies. Nevertheless, in the last decade, new treatment paradigms have emerged including gene therapy, neurotrophic protection and cell replacement therapy. Importantly, while rod and cone photoreceptor death proceeds, the internal retinal architecture remains unaltered for some time, providing a window of opportunity to re-introduce light sensing cells via cell transplantation.

The human retina contains rod photoreceptors and three different types of cone photoreceptors, with rods making up 95% of photoreceptor cells in the retina. Rods are usually found concentrated at the outer edges of the retina and are used in peripheral vision. On average, there are approximately 90 million rod cells in the human retina. Rod photoreceptors are more sensitive than cone photoreceptors and are almost entirely responsible for night vision. Approximately 5-10% of the cone photoreceptor population expresses S-opsin, whereas the majority of cones (90-95%) express either L-opsin or M-opsin light-sensitive proteins. Even though cone photoreceptors are a rare population, forming 2-4% of total retinal cells, humans are dependent on these cells for optimal daylight vision Loss of photoreceptor cells is associated with retinal dystrophies and conditions involving damage to the eye. Furthermore, loss of cone photoreceptor cells, which are crucial for colour detection, central vision and high vision acuity has great impact on sight in retinal degenerative diseases.

Cell replacement therapy is one of several promising future treatment options currently under intense investigation, the goal of which is the re-introduction of healthy cone and rod photoreceptor cells into the degenerating patient retina.

However, many critical challenges exist that prevent the development of cell replacement therapies to replace photoreceptors or cone photoreceptors, including challenges in developing the strategies required for the identification and purification of photoreceptors or cone photoreceptors to allow for cell therapy or transplantation into the eye.

Furthermore, as donor cells are always produced alongside other cell populations, some with potentially detrimental properties, the successful translation of this approach to the clinic is dependent on the development of stringent cell selection and purification methods. For example, while inclusion in donor cell preparations of non-photoreceptors may prevent or hinder establishment of connectivity to host retinal circuitry, presence of mitotically active cell types poses the risk of tumor formation in the host retina after transplantation.

There are currently no photoreceptor or cone photoreceptor purification methods available that would be suitable for human use, as the current methods require genetic manipulation in order to isolate the required cells.

A purification method including CD15-SSEA1− and CD73+ biomarker selection was previously reported in mouse models. However, subsequent experiments with human retinal tissue showed that the combination of markers developed in the mouse model was not directly translatable into the human system, due on the one hand to differences in expression of cell surface antigens between human and mouse retina, and on the other hand to the more ubiquitous expression of biomarkers such as CD73 in the heterogeneous human stem cell differentiation cultures, compared with isolated human foetal retina.

SUMMARY OF THE INVENTION

Through antibody screens (using BD Lyoplates) on foetal human retinal and adult retinal tissue as well as human pluripotent stem cell retinal differentiation cultures the inventors have identified novel retinal expressed biomarkers. They found 72 biomarkers that labelled human foetal retinal cells and 21 biomarkers that labelled discrete cell populations. Co-labelling with AAV2/9 pR2.1.GFP viral vectors identified 20 markers that label foetal cone photoreceptors. Using these novel data, the inventors discovered a panel of endogenously expressed cell surface biomarkers that can be leveraged to gently isolate photoreceptor or cone photoreceptor cells. Examples of cell sorting methods which can be used to isolate the photoreceptor or cone photoreceptor cells include flow cytometry (FACS) or magnetic activated cell sorting (MACS).

The advantage of the surface biomarker purification approaches of the invention are their broad applicability across different cell production platforms, "good manufacturing practice" compatibility and ease of use. As they rely on endogenously present cell surface biomarkers or epitopes, these methods do not require genetic manipulation of the target cells, which before the present invention was the sole available alternative.

The inventors developed a panel of endogenously expressed cell surface biomarkers that can be leveraged to gently isolate photoreceptor cells. A preferred embodiment of the photoreceptor biomarker selection panel comprises two biomarkers for cell depletion, CD29 and CD15-SSEA1, which identify cells that are not of the photoreceptor population, and one marker for positive photoreceptor cell selection that identifies cells of the photoreceptor population, CD73.

Furthermore, the inventors also developed a panel of endogenously expressed cell surface biomarkers that can be leveraged to gently isolate cone photoreceptor cells. A preferred embodiment of the cone photoreceptor biomarker selection panel comprises the combination of three biomarkers for positive cone photoreceptor selection, CD26, CD133 and CD147, and the CD15-SSEA1 biomarker for negative selection.

The death of photoreceptor cells in the retina underlies the vision loss associated with retinal degenerative diseases affecting millions of people worldwide and is at the moment neither preventable nor reversible. This invention enables the isolation and purification of photoreceptor cells or cone photoreceptor cells from populations of cells, such as human pluripotent stem cell (hPSC) culture systems as well as the developing human retina for the purpose of cell replacement therapy, exploration of other therapeutic applications, disease modelling and basic research.

Thus, the invention provides:

A method of identifying photoreceptor cells in a population of cells, comprising the steps of:
  a) determining whether or not cells in the population express CD29 or CD49 on the cell surface;
  b) determining whether or not cells in the population express CD73 on the cell surface; and
  c) identifying a cell as a photoreceptor cell if it is CD29 or CD49 negative and CD73 positive.

The invention also provides:

A method of identifying cone photoreceptor cells in a population of cells, comprising the steps of:
  a) determining whether or not cells in the population express CD29 or CD15-SSEA1 on the cell surface;
  b) determining whether or not cells in the population express at least two of:
    i) CD26, CD133 and CD147 on the cell surface; and/or
    ii) CD57, CD47, CD59, CD200, CD151, CD63, CD98, CD120a, CD81, CD49c, CD90 and CD165 on the cell surface; and
  c) identifying a cell as a cone photoreceptor cell if it is CD29 or CD15-SSEA1 negative and positive for at least two of either:
    i) CD26, CD133 and CD147; and/or
    ii) CD57, CD47, CD59, CD200, CD151, CD63, CD98, CD120a, CD81, CD49c, CD90 and CD165.

The invention also provides a photoreceptor or cone photoreceptor cell population obtained or obtainable by the method of the invention.

The invention also provides a human cell population enriched for photoreceptor cells, wherein photoreceptor cells make up at least 80% of the cells in the population, and wherein the photoreceptor cells have not been genetically manipulated to aid the enrichment.

The invention also provides a human cell population enriched for cone photoreceptor cells, wherein cone photoreceptor cells make up at least 50% of the cells in the population, and wherein the cone photoreceptor cells have not been genetically manipulated to aid the enrichment.

The invention also provides a method of treating retinal dystrophy or a condition associated with cell loss or cell damage in a human eye comprising administering a therapeutically effective amount of the cell population of the invention to a patient.

The invention also provides the cell population of the invention, for use in therapy.

The invention also provides the cell population of the invention, for use in transplantation.

The invention also provides the cell population of the invention, for use in a method or treating retinal dystrophy a condition associated with cell loss or cell damage in a human eye.

The invention also provides a kit for the isolation of photoreceptor cells comprising:
  a) an antibody that binds to CD29; and
  b) an antibody that binds to CD73.

The invention also provides a kit for the isolation of cone photoreceptor cells comprising:
  a) an antibody that binds to CD15-SSEA1;
  b) an antibody that binds to CD26;
  c) an antibody that binds to CD133; and
  d) an antibody that binds to CD147.

Figure 1A:
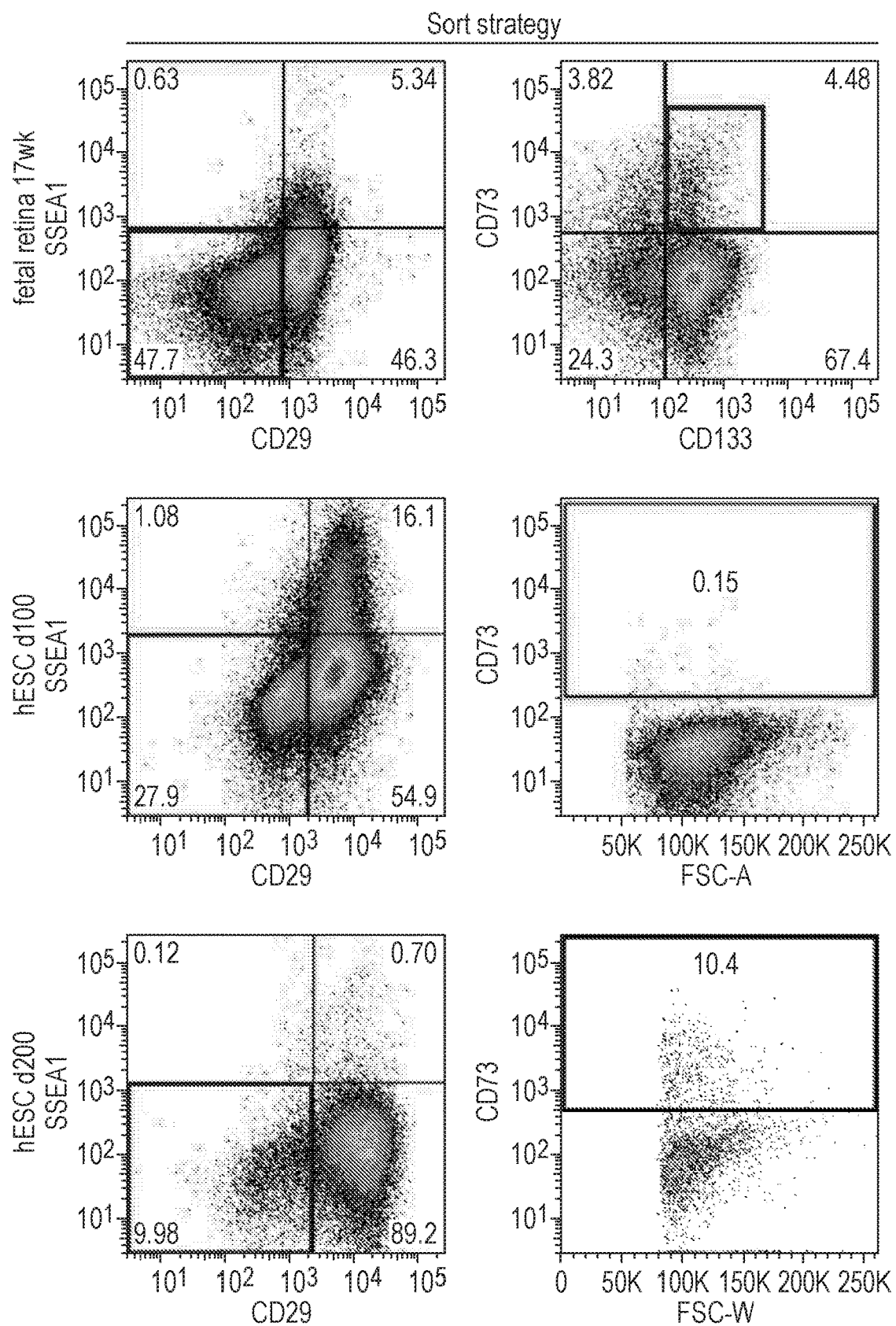
FIG. 1—Cell surface biomarker panel for the isolation of human photoreceptor cells. (A) Sort strategy for isolation of human photoreceptor cells from foetal retinae and pluripotent stem cell (hPSC)-derived retinal organoid cultures. Samples were subjected to CD29/CD15-SSEA1 based double negative selection, followed by positive selection by CD73 alone or in combination with CD133. (B) Immunocytochemical analysis for photoreceptor markers CRX and RECOVERIN in biomarker sorted cells derived from human foetal retinae or hPSC derived retinal organoids. (C-D) Summary of photoreceptor enrichment after biomarker sort. FACS-based dual negative selection (CD29, CD15-SSEA1) or dual negative selection followed by positive selection with CD73 resulted in significant enrichment of human photoreceptors compared to unsorted samples from human foetal retinae (unsorted 23.14%±13.7; CD29/CD15-, 56.83%±15.2; CD29-/CD15-/CD73+, 80.64%±9.44; Mean±SD) as well as hPSC differentiation cultures (unsorted 16.5%±11.64; CD29-/CD15-, 60.82%±14.8; CD29-/CD15-/CD73+, 76.9%±17.4). (D) right panel. Ki67 positive, mitotically active cells are virtually absent after CD29/CD15-SSEA1 dual negative selection in day 100 hPSC derived differentiation cultures (unsorted 13%±5; CD29-/CD15-, <0.1%). Analyses were carried out using foetal retinae ranging from 10-22 weeks post conception (pcw) and hPSC differentiation cultures aged 100-250 days.
Figure 1B:
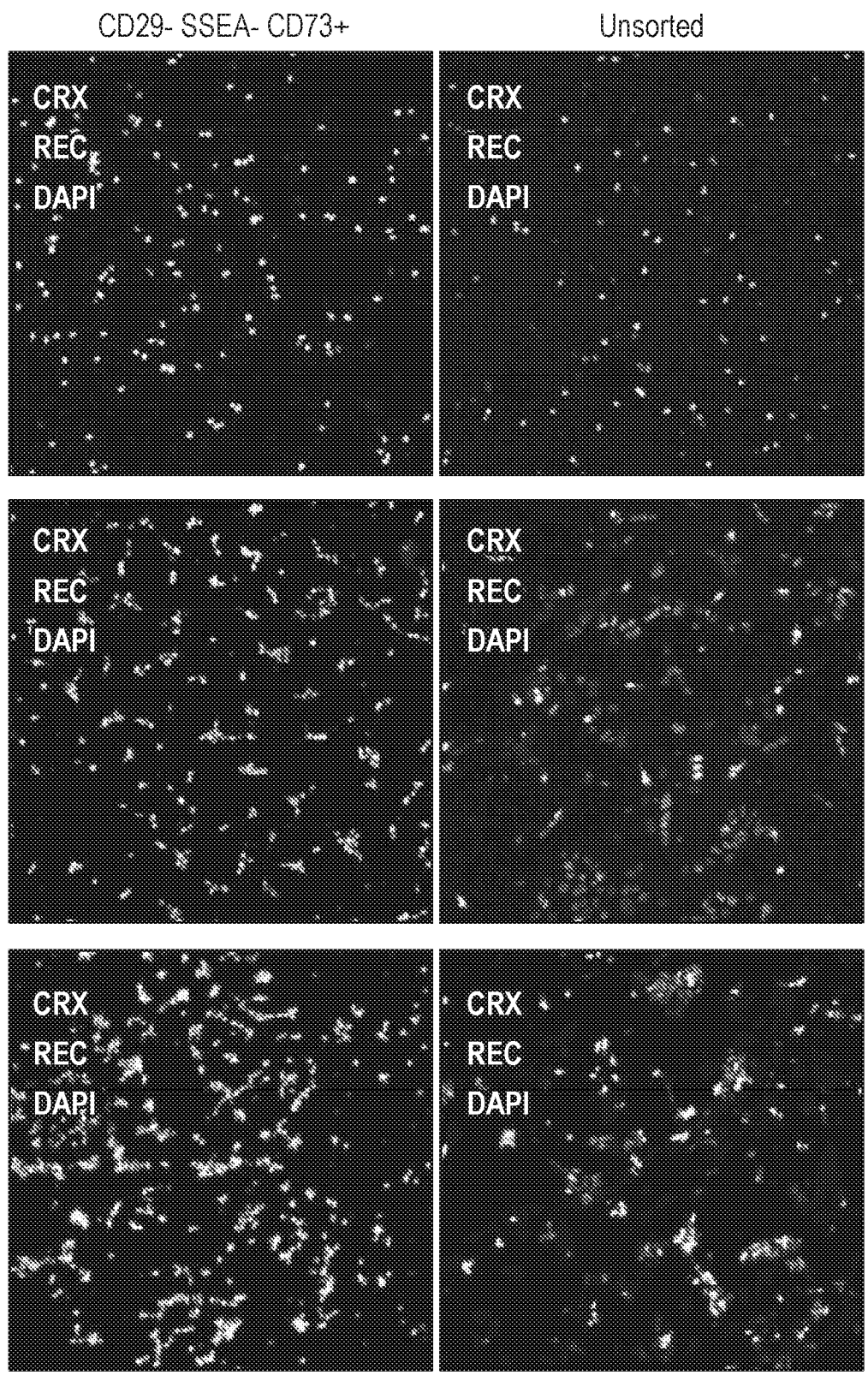
Figure 1C:
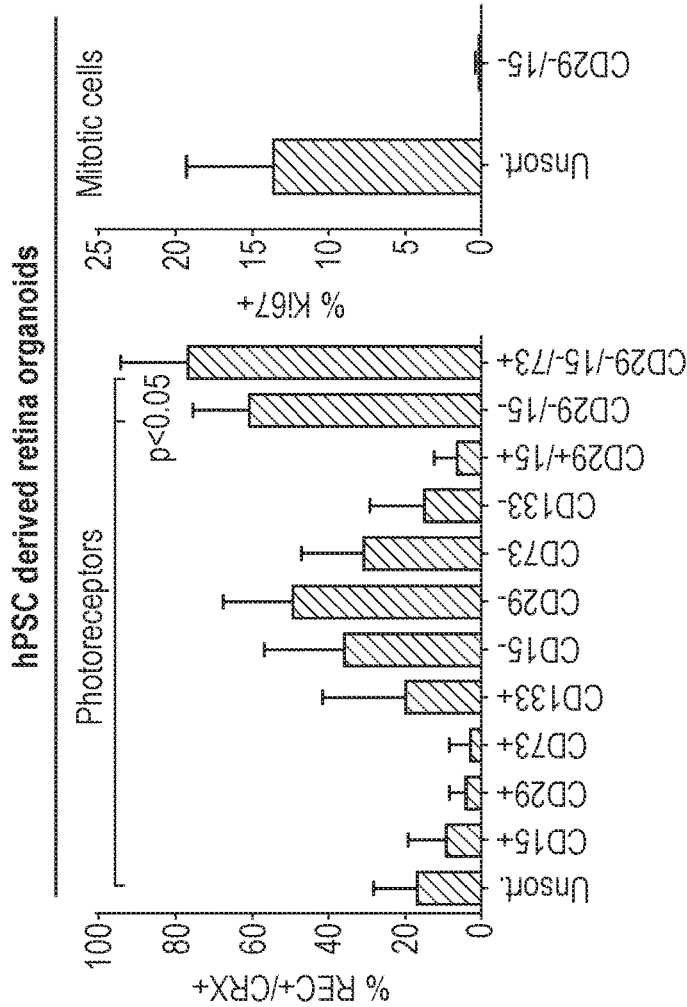

human foetal retina. All 6 cell surface markers identified to label pR2.1.GFP+ve cells from the earlier 12pcw (+7 DIV) human foetal experiment were also expressed in the late foetal retinal samples. Cell surface markers of interest include CD26 and CD147 (black box), which label a high percentage of pR2.1.GFP+ve cells and a low proportion of GFP−ve cells in the late foetal samples. (B) and (C) show the flow cytometry traces of the cell surface markers labelling pR2.1.GFP+ve cells in the early and late foetal retinal samples. CD26 and CD147 (black box) show a clear shift in pR2.1.GFP+ve cells for the late foetal stage. (D) Cell surface marker, CD133, also discretely shifts the pR2.1.GFP+ve cells from human foetal retinal samples (+7 DIV) at the protein level. (E) Representative images of dissociated human foetal retina (17pcw-19pcw) showing co-labelling of L/M-opsin+ cells with CD26, CD133 and CD147 (bottom-most arrow in CD26 image, middlemost arrows in CD133 and CD147 images). Not all L/M-opsin+ve cells express the CD markers (topmost arrow in each image) and the CD markers label additional cells which are negative for L/M-opsin expression (bottommost arrows in CD133 and CD147 images).

FIG. 3. Identifying and profiling of cone cell surface biomarker panel in the human foetal retina. Representative single FAC sorting traces of L/M-opsin cone cell surface markers, (A) CD26 (2.9%±1.6), (B) CD147 (63.6%±12.4) and (C) CD133 (71.1%±7.2) in human foetal retinal samples (18pcw-22pcw; n=4). (D-F) Counting of double positive L/M-opsin and CRX expressing cells reveals a higher percentage of these cells are present in the CD marker+ve population for CD26 (4.9%±2.2), CD133 (1.4%±0.4) and CD147 (1.7%±1.5) compared to unsorted and CD marker-ve cell populations. Representative images are shown from sorting a 19pcw human foetal retina alone with CD26, visually shows the enrichment of L/M-opsin and CRX+ve cells in the CD26+ve cell population (G) compared to the CD26-ve population (H) and unsorted cells (I). (J) Combining the three cell surface markers identified on L/M opsin cones together for FAC-sorting reveals a triple positive cell population within the human foetal retina (P4; n=4). Retinal cells (17pwc-22pcw) were sorted first based on CD133 and CD26 markers: (i) a large proportion of cells are CD133+ve (P5; 52.3%±7.2) and all CD26+ve are additionally CD133+ve which creates a population of double positive cells (P3; 0.6%±0.3). From this double positive cell population, the sorts include triple negative (CD133−, CD26−, CD147−), CD133+ only cells, (CD133+, CD26−, CD147−) and triple positive cells (CD133+, CD26+, CD147+). Analysis of these three populations in addition to the unsorted retinal cells reveals an enrichment of L/M opsin/CRX+ cells in the triple positive cell population (8.7%±9.6) compared to all other cell populations (K). Representative images showing L/M-opsin+ve CRX+ve staining of unsorted cell population (L) compared to the triple positive (CD26+/CD133+/CD147+) cell population (M).

FIG. 4-A-D Identifying and profiling of cone cell surface biomarker panel in the human foetal retina. (A) Representative FACS trace of human foetal retinal samples (n=4) sorted with the cone cell surface biomarker panel, using SSEA1 as a negative selector (Ai) and CD26, CD133 and CD147 for positive selection (Aii-iii). The highest percentage of L/M-opsin/CRX+ve cells within collected cell populations (P7; SSEA1+, P6; CD26−CD133−CD147−/SSEA1−, P5 CD133+CD26−CD147−/SSEA1− and P4; CD26+CD133+CD147+/SSEA1−) was observed within P4 (30.25%±19.7; B). Representative images of L/M-opsin and CRX+ve cells within the unsorted (C) and P4 CD26+ CD133+CD147+/SSEA1− (D) enriched populations.

FIG. 4E-H—Application of cone cell surface biomarker panel in hESC-derived retinal differentiation cultures. A dissociated human embryonic stem cell (hESC)-derived retinal differentiation culture at Week 17.5 (n=1) was sorted using the cone cell surface biomarker panel (CD26/CD133/CD147/CD15-SSEA1), which showed a similar FAC-sorting traces to the human foetal retina (Ei-iii). The percentage of cone arrestin (ARR3) and CRX+ve cells within the CD26+CD133+CD147+/SSEA1− cell population showed an enrichment of cones compared to the unsorted cell population (F). Representative confocal images show the Cone arrestin/CRX+ve cells within the unsorted (G) and P4 CD26+CD133+CD147+/SSEA1− cell populations (H).

DETAILED DESCRIPTION OF THE INVENTION

It is to be understood that different applications of the disclosed methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "cell population" includes "cell populations", reference to "biomarker" includes two or more such biomarkers, and the like.

All publications, patents and patent applications cited herein, whether supra or infra, are hereby incorporated by reference in their entirety.

Throughout the present specification CD15, CD15-SSEA1 and SSEA1 are used interchangeably to mean the same biomarker.

The present invention provides a method for the identification of photoreceptors in a population of cells. The present invention also provides a method for the identification of cone photoreceptors in a population of cells.

The population of cells may be cells from a mammal. Preferably the population of cells are human cells. The population of cells can be human pluripotent stem cells (hPSC) or cells derived from human pluripotent stem cells. The population of cells can be human induced pluripotent stem cells (hiPSC) or cells derived from human induced pluripotent stem cells. The population of cells can be human embryonic stem cells (hESC) or cells derived from human embryonic stem cells. The population of cells can be human foetal retinal cells or cells derived from human foetal retinal cells. The population of cells can be directly converted human somatic cell populations or cells derived from directly converted human somatic cell populations. Mertens et al 2016, for example, provides a definition of direct conversion. Direct conversion can be summarised as the conversion of one somatic cell type to another without the step of producing induced pluripotent stem cells.

The population of cells may be cultured before the methods of identification of the invention. The culturing of the population of cells may allow for the differentiation of cells to the photoreceptor or cone photoreceptor lineage. Methods of culturing the populations of cells described herein are known to the person skilled in the art.

In the identification methods of the invention cells in a population are determined to be positive or negative for the expression of certain cell surface biomarkers. Certain combinations of positive and negative cell surface biomarkers allow for the identification of a cell as a photoreceptor or a cone photoreceptor. A biomarker is defined as a positive selector for photoreceptor or cone photoreceptor identity if it is possible to use the biomarker as an antigen that identifies cells of the photoreceptor and cone photoreceptor lineage in a method of isolation of cells in a population. For example, an antibody binds to the biomarker antigen and allows the cells of the photoreceptor and cone photoreceptor lineage to be isolated and retained.

A biomarker is defined as a negative selector for photoreceptor or cone photoreceptor identity if it is possible to use the biomarker as an antigen that identifies cells that are not of photoreceptor and cone photoreceptor lineage in a method of isolation of cells in a population. For example, an antibody binds to the biomarker antigen and allows the cells that are not of the photoreceptor and cone photoreceptor lineage to be removed.

Thus, in the identification methods of the invention, it is determined whether or not cells in a population express certain biomarkers on their cell surface. A cell is identified as a photoreceptor or a cone photoreceptor if it is positive for the expression of certain cell surface biomarkers and negative for the expression of other cell surface biomarkers.

The cell surface biomarkers used as negative selectors of photoreceptor cells in the photoreceptor identification method of the invention include CD29 (also known as Integrin beta1 protein), CD49 or CD15-SSEA1.

An embodiment of the photoreceptor isolation method of the invention comprises, determining whether or not cells in a population express CD29 and CD15-SSEA1 on the cell surface and identifying a cell as a photoreceptor cell if it is both CD29 and CD15-SSEA1 negative.

The biomarkers used as positive selectors of photoreceptor cells in the photoreceptor identification method of the invention include CD73. In a preferred embodiment of the invention CD29 is used as a negative selector and CD73 is used as a positive selector. In an especially preferred embodiment, both CD29 and CD15-SSEA1 are used as negative selectors.

The cell surface biomarkers used as negative selectors of cone photoreceptor cells in the cone photoreceptor identification method of the invention include CD29 or CD15-SSEA1. The cell surface biomarkers used as positive selectors of cone photoreceptor cells in the cone photoreceptor identification method of the invention include CD26, CD133, CD147, CD57, CD47, CD59, CD200, CD151, CD63, CD98, CD120a, CD81, CD49c, CD90 and CD165. In the cone photoreceptor identification method of the invention, in the positive selection step, at least two of either i) CD26, CD133, CD147; and/or ii) CD57, CD47, CD59, CD200, CD151, CD63, CD98, CD120a, CD81, CD49c, CD90 and CD165 are used. In a preferred embodiment of the invention, CD15-SSEA1 is used as a negative selector and at least two of either i) CD26, CD133, CD147; and/or ii) CD57, CD47, CD59, CD200, CD151, CD63, CD98, CD120a, CD81, CD49c, CD90 and CD165 are used as positive selectors. In an especially preferred embodiment of the invention CD15-SSEA1 is used as a negative selector and at least CD26, CD133 and CD147 are used as positive selectors.

The identification method of the invention may further comprise a step of isolating the identified photoreceptor or cone photoreceptor cells from the population of cells. In a preferred embodiment, the method of isolation is by magnetic-activated cell sorting (MACS) or fluorescence-activated cell sorting (FACS). Suitable isolation methods may involve antibody binding to the cell surface biomarkers used to identify the photoreceptor or cone photoreceptor cells, said antibodies being used as a means to separate out the photoreceptors or cone photoreceptors out from the rest of the population of cells.

The identification method of the invention may also comprise steps of culturing the identified photoreceptor or cone photoreceptor cells after they have been isolated. The post-isolation culturing steps may allow the cells to differentiate into mature photoreceptors or cone photoreceptors. Such methods of culturing cell populations of photoreceptors or cone photoreceptors are known to the person skilled in the art.

The invention also provides photoreceptor or cone photoreceptor cells or cell populations obtained or obtainable by any of the methods of the invention described herein.

The invention also provides human cell populations enriched for photoreceptor cells, wherein photoreceptor cells make up at least 50%, at least 60% or at least 70% of the cells in the population, and wherein the photoreceptor cells have not been genetically manipulated to aid the enrichment. The invention also provides human cell populations enriched for photoreceptor cells, wherein photoreceptor cells make up at least 80% of the cells in the population, and wherein the photoreceptor cells have not been genetically manipulated to aid the enrichment. In a preferred embodiment of the invention, photoreceptor cells make up at least 90% of the cells in the population.

The invention also provides human cell populations enriched for cone photoreceptor cells, wherein cone photoreceptor cells make up at least 20%, at least 30% or at least 40% of the cells in the population, and wherein the cone photoreceptor cells have not been genetically manipulated to aid the enrichment. The invention also provides human cell populations enriched for cone photoreceptor cells, wherein cone photoreceptor cells make up at least 50% of the cells in the population, and wherein the cone photoreceptor cells have not been genetically manipulated to aid the enrichment. In a preferred embodiment of the invention, cone photoreceptor cells make up at least 60%, at least 70% or at least 80% of the cells in the population.

The human cell populations enriched for photoreceptors or cone photoreceptors of the invention are provided as a result of the methods of the present invention. As such, the photoreceptors or cone photoreceptors have not had to be genetically modified in order to identify and isolate them from a population of cells, i.e. have not been genetically modified to aid their enrichment. Before the present invention, there was no way of identifying and isolating human photoreceptors or cone photoreceptors without resorting to genetic manipulation of the cells. Thus, the human cell populations enriched for photoreceptors or cone photoreceptors of the invention are novel. Furthermore, there was no suggestion in the prior art before the present invention that human cell populations enriched for photoreceptors with at least 80% purity or cone photoreceptors with at least 50% purity could be isolated without genetic modification.

The cells or cell populations of the invention may be formulated with any pharmaceutically acceptable diluent or excipient. The cells or cell populations may be present in suspension. The cells or cell population may be grown on a scaffold or substrate. The cells or cell populations may be formulated with additional pharmaceutical agents, including immunosuppressive agents or growth factors. The cells or cell populations may be combined with agents known to plasticize the nervous system, which may enhance the ability of the cells or cell populations to connect to the nervous system and grow into the eye.

The present invention includes a method of therapy comprising administering a therapeutically effective amount of the cells or cell populations of the invention to a patient. The present invention includes a method of transplantation comprising administering a therapeutically effective amount of the cells or cell populations of the invention to a patient. The present invention includes a method of treating retinal dystrophy or a condition associated with cell loss or cell damage in a human eye comprising administering a therapeutically effective amount of the cells or cell populations of the invention to a patient. Examples of retinal dystrophies or conditions include: retinal injury or trauma, retinal degeneration, inherited retinal dystrophy, retinitis pigmentosa, age-related macular degeneration and Leber's congenital amaurosis. In a preferred embodiment of the method of treatment of the invention the cells or cell populations are administered by injection into the sub-retinal space.

The cells or populations of cells of the invention may be used in therapy. The cells or populations of cells of the invention may be used in transplantation. The cells or populations of cells of the invention may be used in the treatment of retinal dystrophy or a condition associated with cell loss or cell damage in a human eye. Examples of retinal dystrophies or conditions include: retinal injury or trauma, retinal degeneration, inherited retinal dystrophy, retinitis pigmentosa, age-related macular degeneration and Leber's congenital amaurosis.

The cells or populations of cells may autologous cells (derived from the eye to be treated), heterologous cells stored in a cell bank, or genetically modified cell lines derived from these cells. The number of cells to be used will vary depending on the nature and extent of damage. Typically, the number of cells used in the methods of treatment or medical uses of the invention will be in the range of about 100,000 to several million. Treatment need not be restricted to a single dose or transplantation. Additional doses provided or transplants may be carried out to further improve function.

The cells or population of cells of the invention may be used as agents to treat retinal dystrophy or a condition associated with cell loss or cell damage in a human eye.

The cells or population of cells of the invention may be used in the manufacture of a medicament for the treatment of retinal dystrophy or a condition associated with cell loss or cell damage in a human eye.

The invention also provides kits for the isolation of photoreceptor cells comprising an antibody that binds to CD29 and an antibody that binds to CD73. In a preferred embodiment, the kit also provides an antibody that binds to CD15-SSEA1.

The invention also provides kits for the isolation of cone photoreceptor cells comprising an antibody that binds to CD15-SSEA1, an antibody that binds to CD26, an antibody that binds to CD133 and an antibody that binds to CD147.

The antibodies present in the kits of the invention may be specific for human proteins. The antibodies present in the kits of the invention may be conjugated to agents that aid in the isolation of cells in methods such as MACS or FACS. The agents may be fluorophores.

EXAMPLES

Example 1

Photoreceptor Identification

Methods

Animals

Experimental mice were kept in University College London animal facilities and all experiments were conducted in agreement with the Animals (Scientific Procedures) Act 1986 and the Association for Research in Vision and Ophthalmology Statement for the Use of Animals in Ophthalmic and Vision Research. C57Bl/6J, and C3H/HeNCrl (RD1; Pde6b$^{rd1/rd1}$) recipient mice at 3 weeks of age at the time of transplantation were obtained from Charles Rivers laboratory.

Human Pluripotent Stem Cell Culture

All pluripotent stem cells were maintained as previously described for hESC cultures. Human embryonic stem cells and induced pluripotent cells were either cultured on a feeder layer of irradiated mouse embryonic fibroblasts (MEFs) in embryonic stem cell medium (DMEM/F12 (1:1), 20% knockout serum replacement, 0.1 mM mercaptoethanol, 1 mM L-glutamine, MEM nonessential amino acids, and 4 ng/mL FGF2) or under feeder-free conditions using mTesR1™ (Matrigel™) or Nutristem® (Laminin 521) media. For feeder-dependent culture hPSCs were passaged every 5-6 days using Dispase and Collagenase, and morphologically identifiable differentiated cells were mechanically removed at each passage. hPSCs cultured in mTeSR1 on matrigel substrate were passaged with RelesR™ reagent, while cells maintained in Nutristem on Laminin 521 were passaged with 1×EDTA as recommended by the manufacturer.

Retinal Differentiation of hESC and hiPSC Cultures

The method for differentiating hiPSC cells toward a retinal fate was carried out according to a previously described protocol (Meyer et al 2009) but with some modification. The differentiation time line and output was approximately the same between different cell lines and independent of maintenance conditions. Briefly, hiPSC cultures were lifted enzymatically using dispase (1 mg/ml) and grown as aggregates/embryoid bodies in EB media for 4 days without FGF2. Embryoid bodies were then transferred to a defined neural induction medium, which consisted of DMEM/F12, 1% N2 supplement, MEM nonessential amino acids, and 2 g/mL heparin. At day 6 of differentiation, EBs were allowed to settle in laminin coated tissue culture plates (6 well) and remained in this configuration for the remainder of the experiment. After 10 days post lifting, neuroepithelial structures were visible within the cultures. On day 16, cultures where switched to chemically-defined retinal differentiation media consisting of DMEM, F12 (3:1) supplemented with 1% B27. In contrast to the originally described protocol, optic vesicle-like structures were not lifted by cutting but remained in the same culture vessel.

Histology and Immunohistochemistry

Retinal organoid specimens or human foetal retinae were fixed in 4% (w/v) phosphate-buffered formaldehyde solution at 4° C. for 15-30 min, washed three times with phosphate-buffered saline (PBS) and equilibrated in 30% (w/v) sucrose solution at room temperature for 1 hours. Specimens were then transferred into an optimal cutting temperature (OCT)-compound (RA Lamb) and frozen in a dry ice-methylbutane slurry. A Leica® CM1900UV cryostat was used to produce 18 µm thick sections, which were collected onto Superfrost™ plus glass slides (VWR). For immunochemical analysis OCT compound was removed by a 15 min incubation in 37° C. PBS and cryosections were blocked with 10% (v/v) FBS, 1% (w/v) bovine serum albumin (BSA) in PBS containing 0.1% (v/v) Triton X-100 for one hour at room temperature. The following primary antibodies were used in the same blocking solution for 1 h at room temperature of 4° C. overnight; Recoverin, Millipore®, 1:1000; Ki67, Abcam®, 1:300; CRX (clone 4G11), Sigma®, 1:1000; Pax6, Covance®, 1:1000; RAX, Abcam®, 1:1000; OTX2, Abcam, 1:200; BRN3b, Millipore/Upstate®; 1:300; AP2a, Hybridoma Bank®, 1:100.

The primary antibody was omitted for negative controls. Primary antibody staining was followed by 3 washes with 1×PBS. Subsequently, cryosections were incubated for 1 h at room temperature with the appropriate secondary antibody diluted in blocking solution (Goat anti-rabbit AlexaFluor594®, Invitrogen®, A-11037, Goat anti-mouse AlexaFluor594, Invitrogen; all 1:800). Hoechst 33342® (1:3000, Sigma-Aldrich®) was applied for 10 min at room temperature to counterstain nuclei, followed by three washes with PBS prior to cover-slipping with the Citifluor™ AF-1 (Electron Microscopy Science) mounting medium.

Dissociation of Human Retinae/hPSC Derived Retinal Cultures and Flow Cytometry

Human retinae or hPSC (ESC or iPSC) derived retinal cultures (for example organoids) were isolated via microdissection and dissociated into a homogenous single cell suspension using a papain based, enzymatic method according to manufacturer's instructions (Worthington Biochemical®, Lorne Laboratories®, UK). Foetal human eyes ranged in age from 12-22 weeks of gestation, whereas hPSC differentiation cultures were harvested at either day 100 or day 200. Dissociated cells were resuspended in flow-cytometry blocking buffer (1% BSA, PBS) and kept on ice for 30 min. Subsequently, conjugated, monoclonal flow antibodies were added to the samples (1×10$^6$ cells in 100 ml) and incubated for 1 h, protected from light. The following monoclonal antibodies were used for FACS-analysis (LSRII) and FAC-sorting (BD FACS AriaIII™) as recommended by supplier: CD73-PECy7, BD®; CD133-PE, Miltenyi®; CD29-BV510, BD; SSEA-1APC, BD; CD90-APC, BD; CD9-APC, BD; CD200-V450; CD49f-BV650; EGFR1-PE, BD; GD2-PE, BD; CD184-PE, BD; SSEA-4-PerCP-Cy5.5. After staining the cells were centrifuged at 300 g for 5-10 min at 4° C. and resuspended in FACS blocking buffer and kept on ice until use. FACS gates were defined according to isotype controls where available and more than 10,000 cells analysed. Compensations were applied using BD FACSDiva™ software using singly stained control samples. Data presented is from at least 3 independent replicates.

Immunocytochemistry on Dissociated and FAC-Sorted Human Pluripotent Stem Cell-Derived and Foetal Retinal Cells Human pluripotent stem cell (ESC or iPSC) derived retinal cultures or foetal human retinae (12-22 wk gestation) were dissociated and sorted via biomarker panel as described above. Post sort cells were spun down at 300 g for 15 min at 4° C. and plated on poly-lysine/laminin coated chamber slides (Labtec®) and allowed to adhere for 30 min at 37° C. Chambers were then washed once with PBS and adherent cells fixed with 4% PFA/PBS for no more than 10 min at room temperature. Following three times washing with PBS, samples were blocked in 10% FBS, 1% BSA/PBS containing 0.1% (v/v) Triton X-100 for 1 h at room temperature. The blocking solution was replaced with staining solution containing primary antibody in 10% FBS, 1% BSA/PBS (0.1% (v/v) Triton X-100). The primary antibody was omitted for negative controls. Finally chambers with adherent cells were incubated for 1 h at room temperature with the secondary antibody diluted in blocking solution (Invitrogen, Goat anti-rabbit AlexaFluor594; Goat anti-mouse 488) and counter stained for 5 min with DAPI (Sigma-Aldrich). The percentage of positive cells in the experimental groups was established by cell counter function, using confocal tile scans; >100 cells were counted from 3 biological replicates for each condition.

Antibody Screen

Human foetal, post-mortem adult and day 90 hPSC derived retinal organoids were harvested and dissociated to single cell suspensions as described above. For BD lyoplate screens the inventors followed the manufacturers' recommendations. All centrifugation steps were carried out at 300 g for 5 min at 4° C. After dissociation, retinal cells were resuspended in BD FACS staining buffer and adjusted to a cell concentration of 10 million cells per 1 ml followed by transfer of the cells into round bottom 96-well plates (BD Falcon™, Cat. No. 351177). 20 µl of reconstituted primary antibody solution was then added to the cells, mixed and incubated on ice for 30 minutes. This was followed by several washing steps with FACS staining buffer (BD Pharmingen™) after which the cells were incubated for 30 min with the appropriate biotinylated secondary antibody. Following several washes, 100 µl of Alexa Fluor® 647 Streptavidin (1:4000, 0.5 ug/ml) was added to each well containing cells stained with the biotinylated secondary antibodies and incubated on ice in the dark for 30 min. Stained cells were then washed 3 times and analysed on a BD FACSCalibur™. At least 30,000 events were collected for the analysis using FACSDiva software.

Microscopy, Image Acquisition, and Processing

A Zeiss® LSM710 (Zen2009, Zeiss) microscope was used for acquisition of confocal images. Images were processed in Zen2009 (Zeiss), Photoshop® CS4 (Adobe®), Illustrator CS4 (Adobe) and FUJI applications. Double-labelling analysis was carried out in Adobe Photoshop CS4.

Transcript Analysis by Quantitative Real-Time Polymerase Chain Reaction (qRT-PCR)

Total RNA was extracted from unsorted or FAC-sorted human cell populations using the RNeasy Mini Kit (Qiagen®, UK). An on-column DNA digest was carried out to eliminate all trace amounts of genomic DNA from the samples. Following quantification of total RNA using a NanoDrop ND-1000 spectrophotometer, cDNA was generated by means of M-MLV-reverse transcriptase (Promega®, USA). Gene expression levels were established for select candidate biomarkers using Applied Biosystems® Taqman PCR reagents and probes on a 7500 Real-Time PCR System according to manufacturer's recommendations. Gene expression data was normalized using GAPDH as a reference. ABI 7500 software 2.0.1. was used to calculate the mean RQ values as well as RQmin and RQmax as measures of variation.

Results

Identification of Cell Surface Biomarkers Expressed in the Developing and Mature Human Retina and hPSC Derived Organoid Cultures The inventors sought to identify a human CD (cluster of differentiation) biomarker set useful for the isolation of human photoreceptor taking advantage of foetal (9, 12, 14, and 17 weeks of gestation) and post-mortem adult retinae.

They screened dissociated whole retinal tissue against 242 well characterized human CD antibodies using the BD lyoplate system as a flow-cytometry high-throughput screening platform. They found 46 biomarkers that were expressed in human retinae at the various stages screened displaying substantial and robust labelling including many that delineated particular cell populations suggesting that they were either cell type or stage specific. Some of these markers may be useful for the isolation of non-photoreceptor cells. Here they focused their efforts on identifying either single or combinations of biomarkers useful for the enrichment of rod and cone photoreceptors.

Generation of Retinal Organoids Using hPSC Cultures

Bone fide human foetal and adult retinae are the gold standard tissue source for studying the development of the visual system in the human context. As the physiological quality of these samples can be variably problematic due to the nature of the tissue collection procedure (termination or post-mortem), human pluripotent stem cell derived retinal organoid cultures represent a useful model system to generate human retinal cell types in a time frame consistent with normal retinal development, and also provide a cell source applicable for cell replacement therapy.

For this study, the inventors produced retinal organoids from human pluripotent stem cells utilizing a previously described differentiation protocol with some modification (Meyer et al 2009). Retinal organoids could be generated from both feeder dependent as well as feeder-free culture systems with comparable efficiency.

After 3 weeks of differentiation, optic vesicle-like (OV) structures became visible within the cultures and pigmentation started appearing in the surrounding cells grown attached to the culture vessel. At 8 weeks in culture, OVs displayed signs of internal lamination and strong pigmentation was now widespread across the culture dish. Transcript analysis revealed that many of the key players of retinal commitment such as PAX6, VSX2, MITF, and SIX6 were strongly expressed in the differentiation cultures. In addition, markers of photoreceptor differentiation e.g. CRX, RECOVERIN and OTX2 were also robustly detected at both transcript and protein levels. CRX/RECOVERIN expressing photoreceptor precursors populated the outer aspects of retinal organoids in this culture system whereas AP2a expressing amacrine cells and BRN3b positive ganglion cells were restricted to the internal surface of the structures. While retinal cell types were often organized in laminated organoids, a substantial proportion photoreceptors and other retinal neurons were located in patches throughout the culture dish, often surrounded by retinal pigmented epithelial cells.

Enrichment of Photoreceptors Cells from hPSC Derived Organoid Cultures Using Cell Surface Biomarkers In order to identify human biomarkers useful for the enrichment of photoreceptors from human stem cell sources the inventors tested candidate markers identified in the antibody screen using the aforementioned hPSC retinal differentiation platform. They focused their efforts on biomarkers that had displayed robust staining patterns of well delineated retinal cell populations as the inventors reasoned that too broadly or too narrowly expressed markers would not have the desired enrichment effect. Of the 16 candidate markers considered (GD2, CD29, SSEA-1, SSEA-4, CD9, CD73, CD133, EGFR, CD90, CD200, CD49f, CD147, CD184, CD107b, CD321, CD142), none showed any photoreceptor enrichment properties in their FAC-sort based screening approach when used alone and for positive selection. Interestingly, CD73, a biomarker previously described by the inventors (Lakowski et al 2011), and others (Eberle et al 2011, Eberle et al 2012), as a good tool for rod photoreceptor isolation in the mouse system was ineffective for this purpose using the hPSC derived retinal differentiation cultures. In fact, positive selection using CD73 resulted in a significant reduction of photoreceptors in the differentiation conditions compared to the unsorted sample (2.7%±5.3 and 16.5%±11.6, respectively). Similarly, FAC-sorting for CD133, another biomarker with known expression in photoreceptors did not yield higher numbers of photoreceptors post selection (CD133+: 19.6%±21; CD133−; 15%±14).

However, the inventors noticed that several biomarkers including CD29 and SSEA-1 significantly enriched CRX/RECOVERIN expressing cells in their negative cell fractions after FAC-sort (49.3%±18 and 35.6%±21 respectively, versus 16.5%±11 unsorted cells, n>9) (FIG. 1). While CD29 always labelled the majority of cells in the differentiation system, SSEA-1 expression was more dynamic being expressed in 30% of cells at day 100 of differentiation and only in 2% of the cells at d200, explaining the superior photoreceptor enrichment properties displayed by negative cell selection using CD29. Using FACS analysis, the inventors observed that while SSEA-1 expressing cells largely co-labelled with CD29, a fraction of SSEA-1 positive cells were consistently CD29 negative, indicating a distinct cell population. Therefore, the inventors next tested if combining CD29 and SSEA-1 for double negative cell selection using FAC-sorting would lead to robust enrichment of CRX/RECOVERIN positive photoreceptors from retinal organoid cultures. Using this approach the inventors saw increased enrichment of photoreceptors in the CD29−/SSEA-1-population (60.8%±14). On the other hand, CD29/SSEA-1 double positive cell fractions were significantly depleted of photoreceptors compared to unsorted samples (6.1%±6 vs 16.5%±11).

Lastly, the inventors hypothesised that, while CD73 on its own was not able to increase photoreceptor yields, combination with CD29/SSEA-1 based double negative selection may increase photoreceptor enrichment from stem cell differentiation cultures. The inventors found that 0.1-1.5% of the cell population at day 100 and 200 showed a CD29−/SSEA1−/CD73+ profile, where CD73 positive cells made up 5% and 35% of the total cell population at day 100 and 200, respectively. Addition of the positive selection step using CD73 (CD73+/CD29−/SSEA1−) to the purification protocol, yielded a higher photoreceptor enrichment (77%±17) compared to CD29 alone (49.3%±18), but not significantly higher than CD29−/SSEA-1− double negative selection (60.8%±14), which gives a cell fraction already highly enriched in photoreceptors. The cell selection mode utilizing all three biomarkers resulted in lower yields of CRX/RECOVERIN positive cells than CD29−/SSEA-1− double negative selection, as the number of CD73 expressing (CD73+/CD29−/SSEA1−) photoreceptors was low in the culture system at the stages tested, consistent with a less mature stage of photoreceptor differentiation (FIG. 1).

Verification of Candidate Biomarkers in the Developing and Mature Human Retina

The inventors also tested the candidate biomarkers for their ability to enrich immature photoreceptors from foetal human retinal tissue aged 10-22 weeks of gestation. In contrast to the hPSC derived organoid culture system, neither CD29 nor SSEA-1 negative selection alone resulted in significant enrichment of CRX/RECOVERIN positive photoreceptors post FAC-sorting (14.6%±2.2 and 13.6±1.7, respectively vs 23.1±13 unsorted). By contrast FAC-sorting for CD73 significantly enriched photoreceptor cells, although it labelled less than 5% of the retinal cells during the 10-22 wks developmental period (56.6±30). Like in the hPSC differentiation system, CD29−/SSEA-1− double negative selection with or without additional CD73+ positive selection yielded higher photoreceptor yields from this cell source. Combination of all three biomarkers was superior in terms of photoreceptor cell enrichment compared to double negative selection using CD29/SSEA-1 alone (80.6±9 vs 56.8±15, respectively), although overall cell yield efficiencies were reduced (FIG. 1).

Removal of Mitotically Active Cells Via Biomarker Selection

Figure 1D:
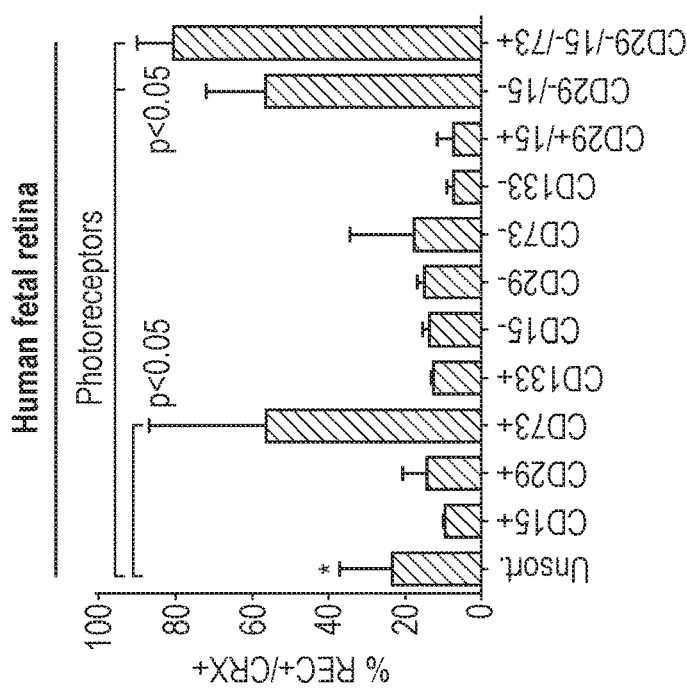

The inclusion of proliferative cell populations such as undifferentiated pluripotent stem cells or progenitor cells in cell preparations for cell therapy applications present a high safety risk owing to their ability to divide rapidly and form tumours in the sub-retinal space of patients following transplantation. It is therefore important that any cell selection strategy would need to ensure that these cells be removed prior to transplantation into patients with retinal dystrophy, not only to exclude the risk of tumour formation but also to better facilitate synaptic connectivity of graft photoreceptors to the host bipolar cells. The inventors tested the ability of the human biomarker panel to remove mitotically active cells from hPSC organoid cultures at day 100 of differentiation. In these experiments, 13.6%±5 of cells in the differentiation cultures stained positive for Ki67, a marker of actively dividing cells that were mutually exclusive with the photoreceptor marker CRX (FIG. 1D). FAC-sorting using CD29/SSEA-1 double negative selection alone was sufficient to remove 98% (0.29%±0.19) of the mitotic cells from the cell suspension, while the remaining cells almost entirely expressed the CRX transcription factor. These data show that mitotically active cells can be efficiently eliminated from hPSC derived donor cell preparations, prior to transplantation, by using the combination of photoreceptor cell surface biomarkers for negative cell selection.

Conclusions

The CD73+ only selection does not achieve sufficient purity levels (see FIG. 1). In addition the known CD15− selection is also limited as the expression level of CD15 is modest and decreases with samples maturity, whereas the novel marker CD29 labels the majority of the cells at all time. The data shows that CD29 is the main driver behind photoreceptor enrichment when used for cell depletion, and combination with SSEA-1 as a second negative selector or with CD73 for positive selection confers a higher photoreceptor purity, albeit with lower overall yields The level of purity of photoreceptor cells achieved for human cells is suitable for clinical application: 80.64%±9.44 (mean±SD).

The inventors have also shown that biomarker sorted donor cells isolated from hPSC derived organoid cultures survive after sub-retinal transplantation into wild-type and RD1 mutant mouse retinae.

Example 2

Cone Photoreceptor Identification

Methods

Human Foetal Tissue Preparation

Human foetal eyes were obtained from the Wellcome Trust and Medical Research Council Funded Human Developmental Biology Resource (http://www.hdbr.org/). Human adult eyes were obtained from Moorfields BioBank.

Human Foetal Retinal Explant Cultures

Human foetal eyes were dissected in sterile conditions and all ocular tissue was removed in order to obtain retina. Intact human foetal retina were cultured free floating in 12 well plates with retinal differentiation media (RDM) containing DMEM-F12, Glutamax, 1×N2, 1×B27 neural supplements (Invitrogen), 10% FBS (Invitrogen) and 1.5× penicillin/streptomycin (Invitrogen). Cell culture media was changed every 2 days.

iPSC Maintenance and Retinal Differentiation

Human iPSCs were cultured in 6 well plates on gelatin with irradiated mouse embryonic fibroblast layer (IRR MEFs; GlobalStem®; 150,000 IRR MEFs per well) and passaged using enzymatic treatment of collagenase and dispase. Knockout serum replacement (KSR) medium with 4 ng/ml fibroblastic growth factor (FGF) was replaced every day. Retinal differentiation of iPSC was based on the protocol developed by the Gamm laboratory (Meyer et al., 2009) but without lifting the optic vesicle structures. Briefly, iPSCs were lifted on Day 0 and transferred into T25 flasks containing KSR medium without FGF to induce the formation of embryoid bodies (EBs). Medium was changed daily before substituting into neural induction medium (NIM) containing DMEM/F12 1:1 (Gibco®), MEM non-essential amino acids on Day 4. To promote neural rosette formation, EBs were transferred onto laminin (30%) coated plates in NIM on Day 6. EBs normally attached to laminin coated plates and formed neural rosettes by Day 8/9. Cultures were then fed every 2 days with NIM until Day 16, where the media was substituted for retinal differentiation media (RDM). Optic vesicle structure was visible from Day 18-20 onwards and media was changed every 2-3 days. FBS was added to cultures at week 14 for late stage cultures.

AAV2/9.pR2.1:GFP Production and Application 293T cells were cultured in D10 medium containing DMEM+Glutamax, 10% FBS and 1× penicillin/streptomycin in 150 cm plates and grown to 80% confluency. pd10-ML-eGFP maxiprep, pHGT1 helper vector, AAV2/9 capsid were transfected into 293T cells using polyethylenimine (PEI) in DMEM and cultured for 24 hrs. After 72 hours, transfected cells were harvested and subjected to four thaw-vortex-freeze cycles to release the virus. Virus lysate underwent benzonase treatment and was prepared for purifications through multiple centrifugation steps and sequential filtering with 5 μm, 0.45 μm and 0.22 μm PES membranes. Virus was purified via ion exchange chromatography and concentrated using a Vivaspin 4 concentrator. Viral genomic titer was determined through qPCR and the virus titer used in this study ranged from $1.48 \times 10^{13}$-$1.01 \times 10^{14}$.

Virus was added to human foetal retinal explant and iPSC-derived retinal differentiation cultures at an MOI between 40,000-45,000 in a minimal volume of media (250 μl for foetal explants and 1 ml for iPSC-derived retinal cultures) and cultured overnight. Additional culture media was added after 12 hrs and completely replaced after 36 hours of culture. Human tissue was cultured for 7 days total, with media replaced every 2 days.

RNA Sequencing

For RNA, retinal tissue was processed with the mirVana RNA extraction kit according to manufacturer's recommendation. Samples were then analysed on the Bioanalyser or Tapestation to assess RNA concentration and quality. All RNA samples were amplified using the SMART-Seq® v4 Ultra Low Input® RNA kit (Clontech Laboratories®) and cDNA libraries were prepared using the Nextera® XT DNA Library Preparation Kit (Illumina). cDNA quality was assessed using Qubit and normalised before sequencing using Illumina® NextSeq500® system; a sequencing depth of 17 million 43 bp paired end reads was performed for all samples. FASTQ files containing raw RNA seq data was aligned using Illumina RNA Seq STAR alignment tool (version 1.1.0) to reference genome hg19, in order to generate BAM files, which were imported into NGS Strand. All samples were normalised using DeSeq method within NGS Strand and all RNA seq data was completed using the same software.

Histology and Immunohistochemistry

For cryosectioning, the whole human eye with the lens removed was fixed overnight at 4° C. in 4% PFA, before washing three times phosphate-buffered saline and equilibrating in 30% (w/v) sucrose solution for cryo-protection at room temperature until eyes sunk. Samples were then embedded in optimal cutting temperature-compound (OCT) and orientated, before freezing in a methylbutane-dry ice slurry. Tissue sections were cut to 12-16 m thickness using the Leica CM1900 UV cryostat and collected on Superfrost™ plus glass slides (VWR). For immunohistochemistry, retinal sections were washed in PBS for 10-15 minutes at 37° C. to remove the OCT compound and incubated in blocking solution (10% goat or foetal bovine serum, 1% bovine serum albumin in PBS with 0.1% Triton X-100) for 1 hour at room temperature. Sections were incubated with primary antibody for 1 hr at room temperature or overnight at 4° C. Primary antibody was omitted for negative control sections. Sections were washed three times in PBS for 5 minutes, before applying the secondary antibody for 1 hour at room temperature. Sections were washed 3 times with PBS for 5 minutes prior to DAPI (1:3000) incubation at room temperature for 3-5 minutes, which allows for the visualisation of cell nuclei. Sections were washed again in PBS, before applying with Citifluor AF-1 mounting medium and 1.5 coverslips. The same immunostaining procedure was conducted with wholemount foetal retina, however samples were free floating throughout the whole procedure, before being transferred to microscope slides for imaging.

Immunocytochemistry

Retinal cells were fixed in 4% PFA for 5 mins at 37° C. prior to a further 15 mins incubated in 2% PFA/30% sucrose at room temperature. Cells were washed three times in PBS and blocked for 1 hour at room temperature in 1% (w/v) BSA in PBS. Primary antibodies (L/M-opsin, Millipore, 1:400, CRX, Abcam, 1:800; cone arrestin, Novusbio®, 1:100) were added on to cells and incubated for 1 hour at room temperature. For CD marker staining (PE-conjugated CD26, 1:500, BD Biosciences; PE-Vio770-conjugated CD133, 1:500, Miltenyi Biotec; PerCP-Cy5.5-conjugated CD147, clone 1:500, BD Biosciences) on dissociated cells, Triton X-100 was omitted from blocking solution. Cell were washed with three times in PBS and incubated for a further hour with secondary antibodies (Goat anti-rabbit AlexaFluor 594 or Goat anti-mouse 488, Invitrogen, 1:800). DAPI incubation and mounting procedure was performed as previously described in immunohistochemistry section.

Dissociation of Live Retinal Samples and Fluorescence-Activated Cell Sorting (FACS) of Foetal Retinal Cells Labelled with AAV2/9.pR2.1:GFP Human tissue was dissociated using the papain dissociation system (Worthington Biochemical, Lorne Laboratories, UK) according to manufacturer's protocol. Foetal human retinal explants electroporated or infected with cone reporter constructs were dissociated via the papain dissociated method and resuspended in 500 µl 1% foetal bovine serum (FBS)/DMEM. DAPI was added to samples prior sorting to allow the determination of live cell population. The MoFlo XDP cell sorter (Beckman Coulter) was used to isolate live GFP+ cells, which were collected in 3 ml of 50% FBS/DMEM. Cells were then centrifuged at 300×g for 5 minutes at 4° C. and RNA was extracted.

BD Lyoplate Screening Panel Protocol

Retinal samples were dissociated using papain dissociation kit as previously described and resuspended in BD Pharmingen Stain Buffer+EDTA. The supplier protocol was then followed to complete the lyoplate experiments. The recommended number of cells to use for flow cytometric analysis is between 500,000 to 1,000,000 cells per well, however the inventors were able to run significantly less. All washing steps of the protocol involved the addition of 100 µl of BD Pharmingen Stain Buffer+EDTA and centrifuge at 300×g for 5 minutes. This step was then repeated but with 200 µl of BD Pharmingen Stain Buffer+EDTA.

Cells were aliquoted into 3× round-bottom 96 well plates (1001 per well). Primary antibodies of the lyoplate screening panel were reconstituted in 1×PBS and 201 of each antibody was then added to the cells and incubated for 30 minutes at on ice. Primary antibody was omitted for negative control and wells were allocated for IgG/IgM positive control. Cells were then washed, resuspended in 1001 of secondary antibody solution and incubated on ice for 30 minutes in the dark. Subsequently, cells were washed and centrifuged before being resuspended in 150 µl of BD Pharmingen Stain Buffer+EDTA. Samples were then analysed using the BD FACSCabilur. Between 15,000-20,000 events were collected per well and results were analysed using the FlowJo software.

Flow Cytometry and FACS

For cone CD marker sorting, cells were counted and resuspended in blocking solution at a concentration of $1\times10^6$ cells per 100 µl. After incubating cells for 1 hour on ice, conjugated antibodies (PE-conjugated CD26, clone M-A261, BD Biosciences; PE-Vio770-conjugated CD133, clone 293C3, Miltenyi Biotec; PerCP-Cy5.5-conjugated CD147, clone HIM6, BD Biosciences) or isotype controls were added to cells using the manufacturer's recommendations and incubated for a further 1 hour on ice in the dark. Cells were subsequently centrifuged at 200×g for 5 mins at 4° C., before washing in PBS and resuspended in blocking solution for sorting. The MoFlo XDP cell sorter (Beckman Coulter) was used to isolate cells, which were collected into 50% FBS/DMEM media. Isotype and unstained controls were used to set gates and apply necessary compensation. Post sort, cells were then centrifuged at 300×g for 15 minutes at 4° C. and cells for immunocytochemistry were plated out on to pre-coated poly-L-lysine (Sigma) and laminin (Sigma) chamber slides at a cell density 150,000-200,000 cells. For populations where a small cell number had been obtained, all cells were plated out.

Microscopy and Image Processing

Immunofluorescence staining was analysed using Axiovert 135 (Zeiss) microscope with a ProgRes C14 digital camera using OpenLab software (PerkinElmer Life®). Brightfield and fluorescent images were captured using an inverted microscope Olympus® IX71 (Carl Zeiss, Jena, Germany) with a Hamamatsu® ORCA-ER digital camera (Hamamatsu Corp., Bridgewater, NJ). Brightfield images of retinal differentiation cultures were captured using EVOS® XL Core imaging system (Life technologies). Z-28 projection images of retinal sections and wholemounts were acquired using the Zeiss LSM710 (Zen2009, Zeiss) microscope. Images were processed using Zen2009 (Zeiss), ImageJ and Illustrator CS6 (Adobe) applications.

Results

Identification of Cell Surface Markers Expressed on Human L/M-Opsin Cones

The inventors defined the progressive appearance of L/M opsin-expressing human cones cells in the human foetal retinal and the paucity of early human cone markers and sought to isolate and characterise the complete transcriptome of these cells. They used an adeno-associated virus system (pseudotype 2/9) to deliver a GFP reporter construct driven by the previously characterised pR2.1 promoter to human foetal retinal samples in order to label L/M-opsin cone photoreceptors. The pR2.1 promoter consists of a highly conserved locus control region (LCR) and additional enhancer regions found upstream of both L- and M-opsin genes located on the X chromosome in a tandem array (Nathans et al., 1989, Wang et al., 1992). The pR2.1 promoter has been previously demonstrated to drive specific reporter expression in L/M-opsin cone photoreceptors of the canine (Komaromy et al., 2008) and rat retina (Li et al., 2008), but also within S-opsin cones of the mouse retina (Wang et al., 1992, Fei and Hughes, 2001).

Cryosections from 12pcw and 14pcw (+7 DIV) retinal explants revealed the AAV2/9.pR2.1.GFP construct labelled cells of the ONL, which specifically co-label with the L/M-opsin. These cells were also positive for photoreceptor marker, early cone-specific markers, RXRG, but were negative for S-opsin and NR2E3, markers of S-cones and rod photoreceptors and the proliferation marker Ki67, indicating specificity of the reporter virus to post-mitotic L/M-opsin cone cells.

The inventors labelled early (n=4) and late (n=4) human foetal retinal samples with the AAV2/9 pR2.1:GFP virus and used fluorescence-activated cell sorting (FACS) to isolate the GFP+ve and GFP−ve cells for RNAseq to identify the highly expressed and enriched genes of the human L/M-opsin cone transcriptome.

The generated RNAseq data was used to identify the cell surface markers of developing cones, as these provide tools to improve the generation, identification and purification of human cone photoreceptors. Sets of significantly upregulated genes from human foetal GFP+ve samples were analysed using bioinformatics tools, which revealed 31 potential cell surface markers expressed in the late foetal GFP+ve cells. The inventors also searched directly within this gene set for known CD markers. This analysis identified CD markers and non CD markers potential cell surface markers.

In addition to the transcriptomic analysis for surface markers, the inventors used a proteomic approach to assess which CD marker genes gave rise to epitopes, which can be recognised by monoclonal antibodies. The inventors screened for 242 different CD marker antibodies that could be expressed in human L/M-opsin foetal cones by applying 12pcw and 17pcw human foetal retinae labelled with the AAV2/9 pR2.1.GFP reporter on to BD lyoplate high throughput antibody-antigen screening panels.

The inventors defined the detection of CD markers labelling pR2.1 GFP+ve cells as: i) labelling at least 50% of the pR2.1 GFP+ve cell population and; ii) causes a discrete shift of the pR2.1 GFP+ve cells. This screening method revealed 6 CD markers that shifted the 12pcw pR2.1.GFP+ve cell population (CD57, CD47, CD59, CD151, CD200, CD98; FIGS. 2A and B), while 14 CD markers were discovered labelling 17pcw pR2.1.GFP+ve cells (CD57, CD47, CD59, CD200, CD151, CD63, CD98, CD26, CD147, CD120a, CD81, CD49c, CD90, CD165; FIGS. 2A and C).

All CD markers present in the 12pcw pR2.1.GFP+ve cell population were expressed in the 17pcw pR2.1.GFP+ve cells, however these markers appeared to label the majority of both GFP+ve and GFP−ve cell populations. Additional markers were detected in the late foetal sample, which suggests the expression of CD markers expressed in cones increases during development (FIG. 2A).

Figure 2C:
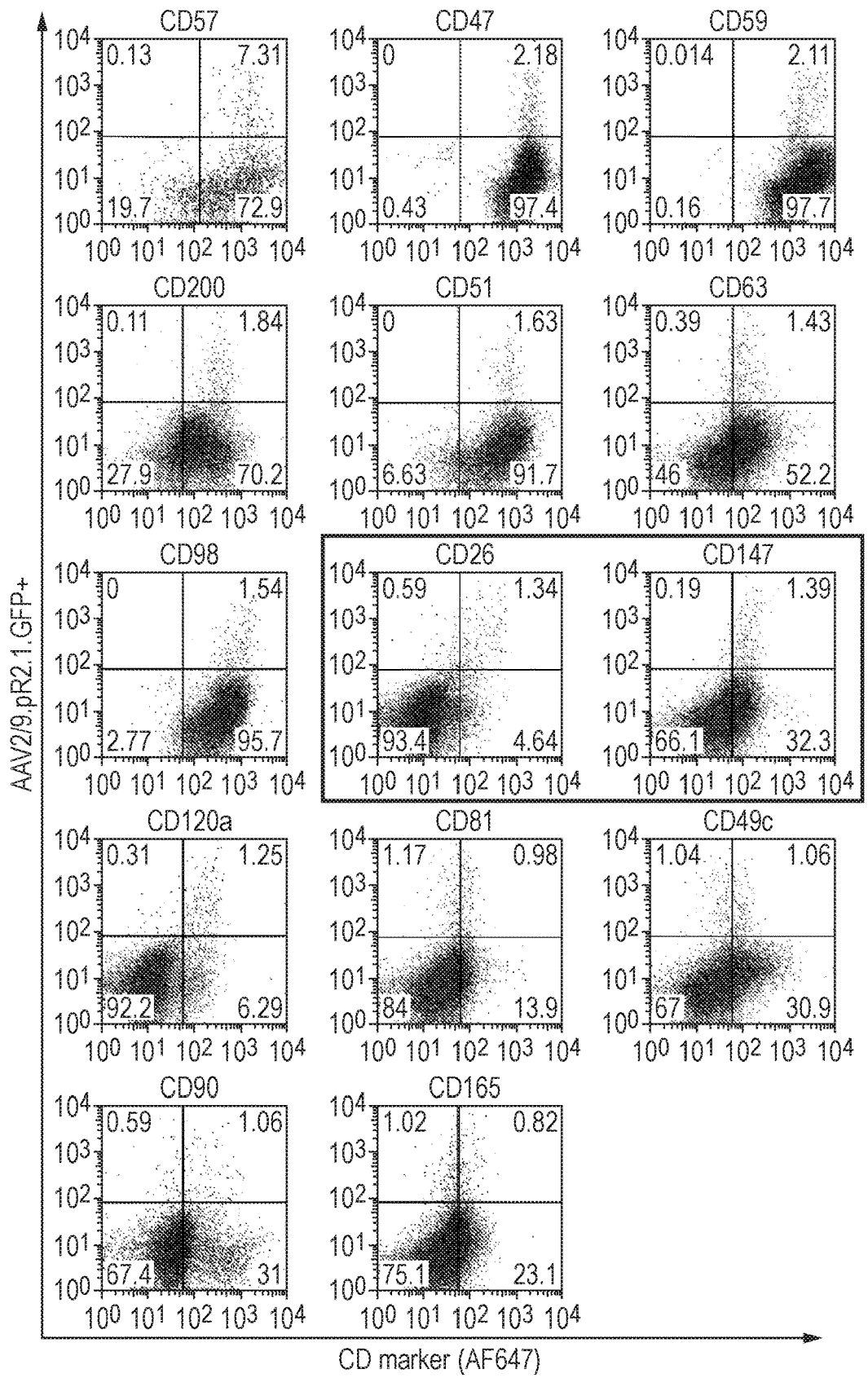
FIG. 2—Cell surface marker expression in human foetal AAV2/9.pR2.1.GFP labelled cells. Human foetal retinal samples labelled with the AAV2.9.pR2.1.GFP reporter were dissociated and applied on to human BD lyoplate screening panels containing 242 different cell surface marker antibodies. Criteria for cell surface markers labelling pR2.1.GFP+ ve cells included at least a 50% discrete shift of the cell population and a small shift in GFP-ve cells. (A) The table shows the 14 cell surface markers identified to label pR2.1.GFP+ve cells from a 17pcw (+7 DIV (days in vitro))

Notably, some of these CD markers displayed greater specificity to pR2.1.GFP labelled cells at the later foetal timepoints, i.e. labelling a higher percentage of GFP+ve cells and lower percentage of GFP−ve cells, which include markers CD26 and CD147 (FIGS. 2A and C; black boxes). Both these markers showed a discrete labelling and shifting of the pR2.1.GFP cell population (CD26 GFP+ve 73.3%, GFP−ve 6.83%; CD147 GFP+ve 68.9%, GFP−ve 39.6%), in comparison to other markers such as CD81 and CD49c which although showing labelling of pR2.1.GFP cells do not cause a discrete shift (FIG. 2C). CD26 and CD147 were upregulated in the late foetal pR2.1.GFP labelled cells from the total RNA seq data.

Figure 2D:
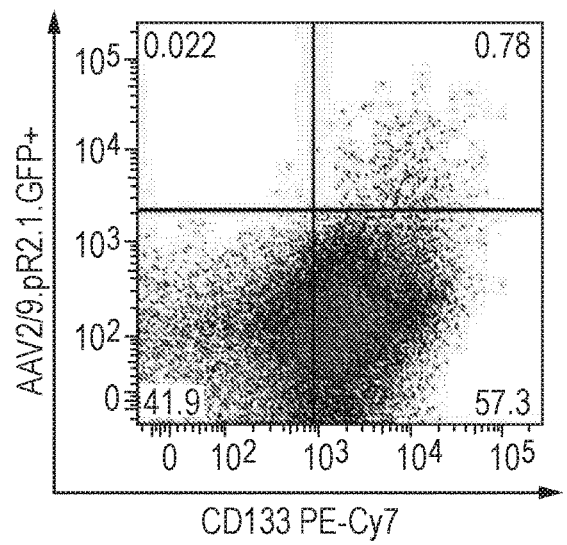
Figure 2E:
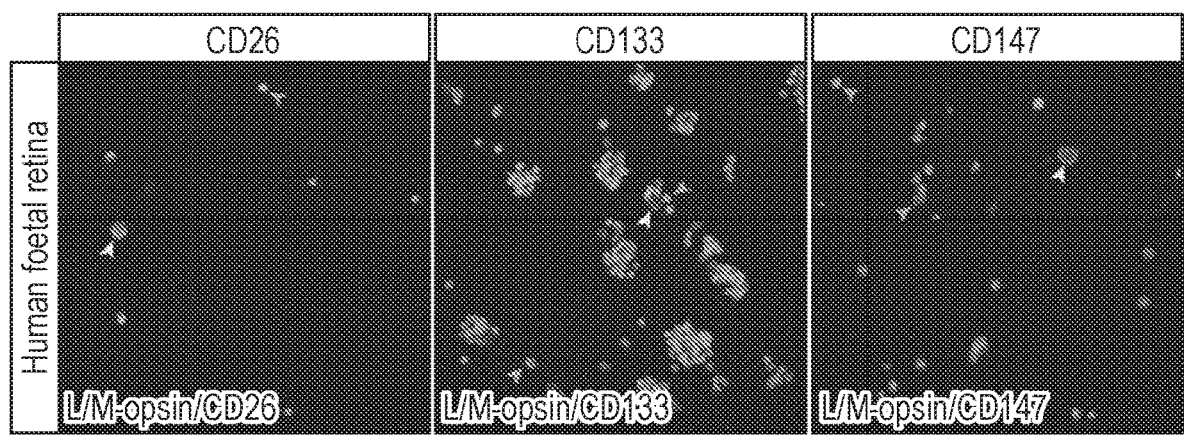

Flow cytometry data revealed Prominin-1 (CD133), which featured in the significantly upregulated genes from the late human foetal pR2.1.GFP+ve transcriptome data and has been previously used within a biomarker panel in the mouse retina to isolate photoreceptor cells (Lakowski et al 2015), also robustly shifts 13pcw and 14pcw pR2.1.GFP cells at the protein level (FIG. 2D).

From these transcriptomic and proteomic data sets, the inventors selected CD markers CD26, CD147, and CD133, as a preferred biomarker panel combination to positively enrich for L/M-opsin cone photoreceptor via a cell sorting strategy. In addition to this positive selection of LM-opsin cones, the inventors further added SSEA-1 (CD15) to the panel which showed no expression by human pR2.1.GFP+ cells in the human lyoplate screening experiment and has been previously used as negative selecting marker to remove undesirable cells, such as mitotically active retinal progenitor cells (Lakowski et al., 2015).

To determine if these CD markers could be used in an L/M-opsin cone cell enrichment strategy, human foetal retinal samples were FAC-sorted with conjugated CD marker antibodies in isolated and in combination, before being plated down, stained with the L/M-opsin and CRX antibody and counted (FIG. 3). The proportion of CD marker+ve cells labelled by CD147 (63.6%±12.4) and CD133 (71.1%±7.2%) exceeded the expected size of the cone photoreceptor population in the human retina, which in the adult retina is approximately 2-3%, however the percentage CD26+ve cell population CD26+ve cell (2.9%±1.6) showed an equivalent size to the estimated proportion of cone photoreceptors in the human retina (FIG. 3A-C). The CD marker+ve cell populations generally showed a greater percentage of L/M-opsin and CRX+ve cone photoreceptors compared to unsorted cells and CD marker-ve cells (FIG. 3D-F), which could readily be observed from sorting human retinal samples with CD26 (FIG. 3G-I).

Figure 3G:
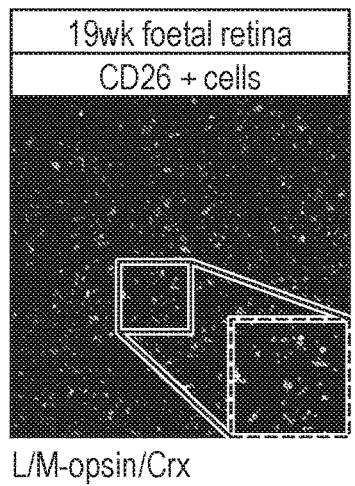
Figure 3H:
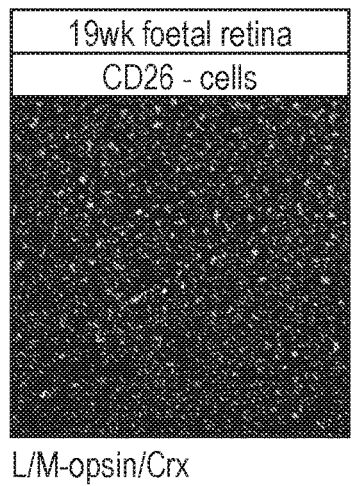
Figure 3I:
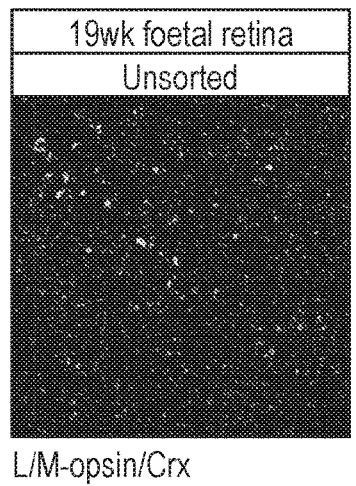
Figure 3J:
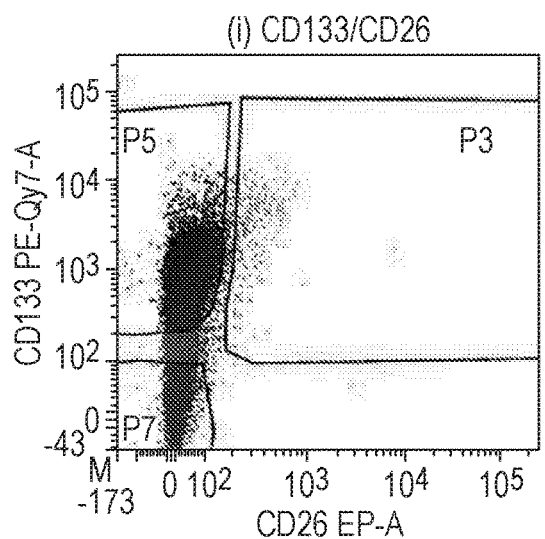
Figure 3J:
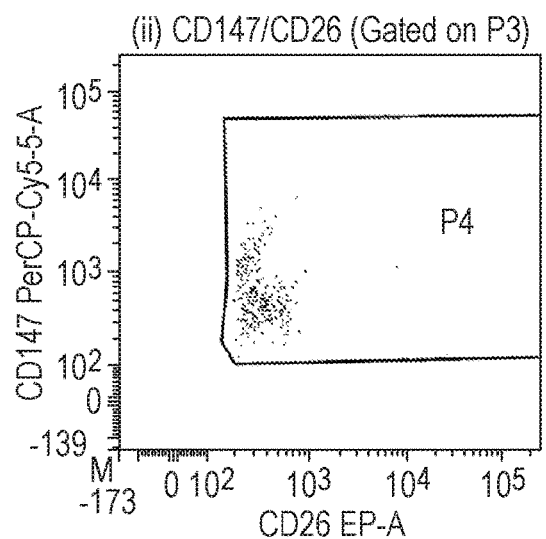
Figure 3K:
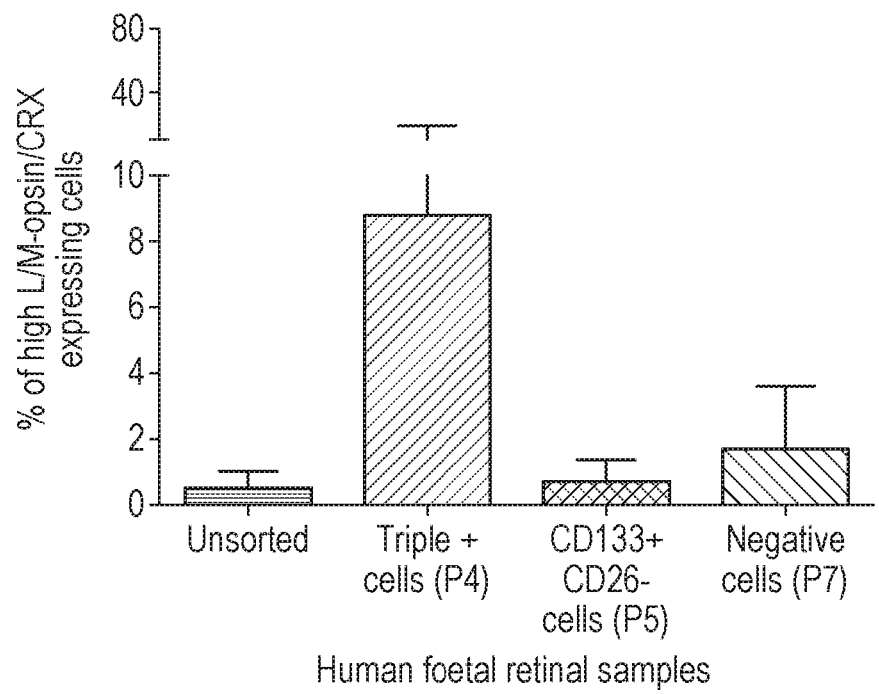
Figure 3L:
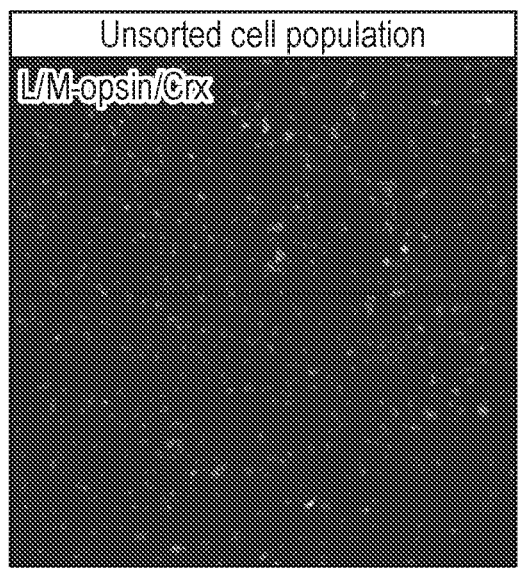
Figure 3M:
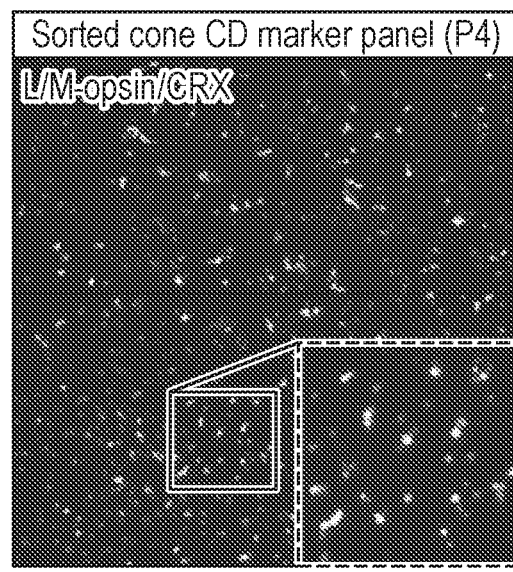

Combining the three cell surface markers identified on L/M opsin cones together for FAC-sorting revealed a triple positive cell population within the human foetal retina (P4; n=4). Retinal cells (17pwc-22pcw) were sorted first based on CD133 and CD26 markers: (FIG. 3Ji) a large proportion of cells are CD133+ve (P5; 52.3%±7.2) and all CD26+ve are additionally CD133+ve which creates a population of double positive cells (P3; 0.6%±0.3). From this double positive cell population, the sorts include triple negative (CD133−, CD26−, CD147−), CD133+ only cells, (CD133+, CD26−, CD147−) and triple positive cells (CD133+, CD26+, CD147+). Analysis of these three populations in addition to the unsorted retinal cells revealed an enrichment of L/M opsin/CRX+ cells in the triple positive cell population (8.7%±9.6) compared to all other cell populations (FIG. 3K).

Figure 4A:
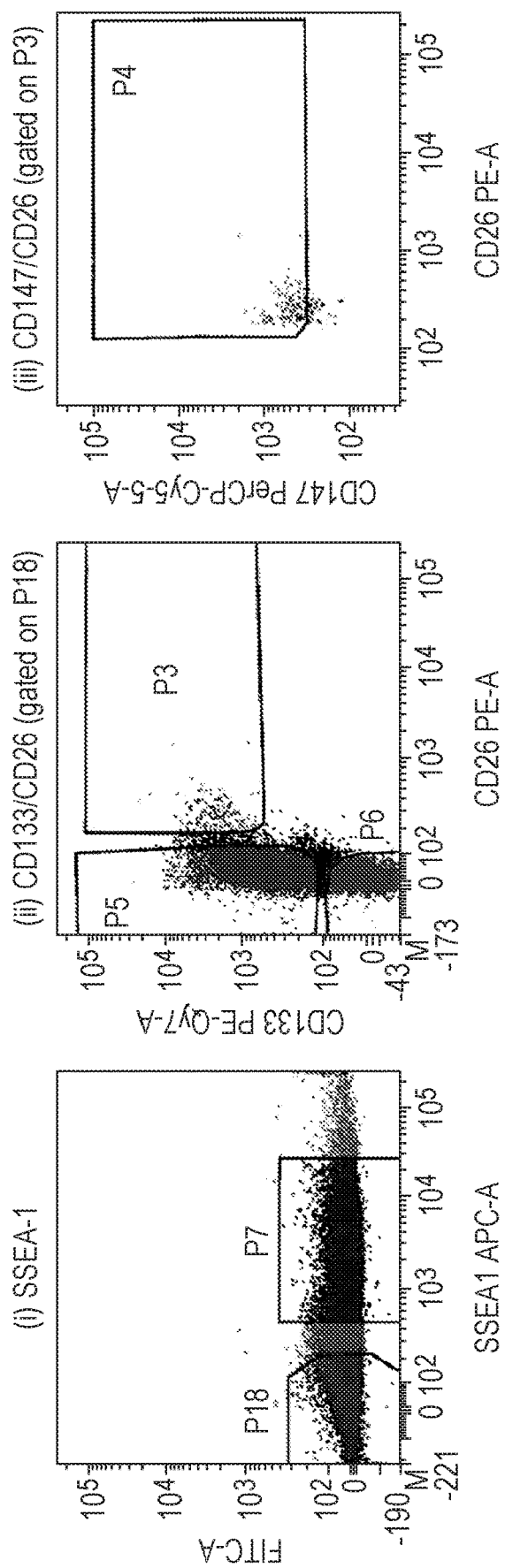
Figure 4B:
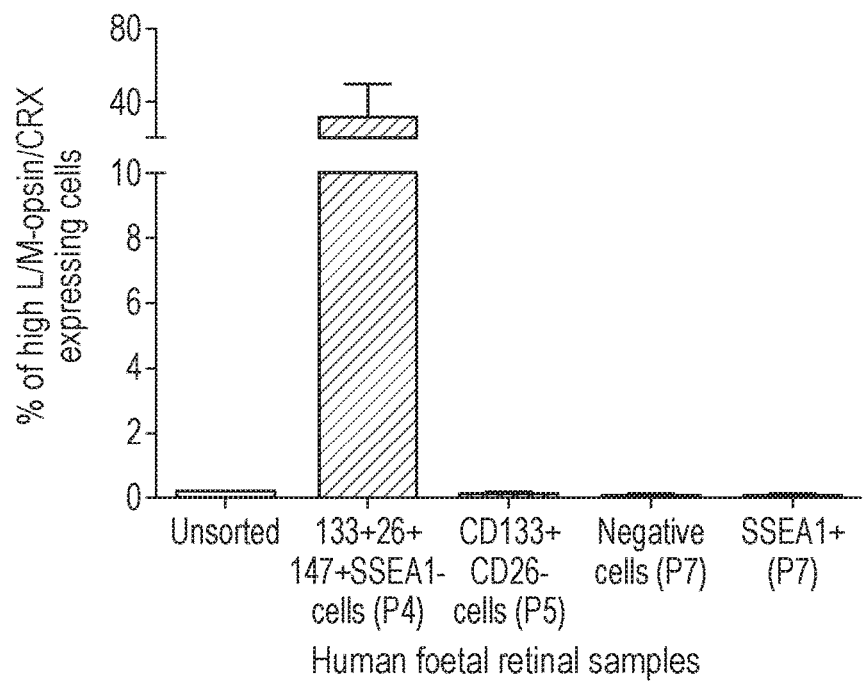
Figure 4C:
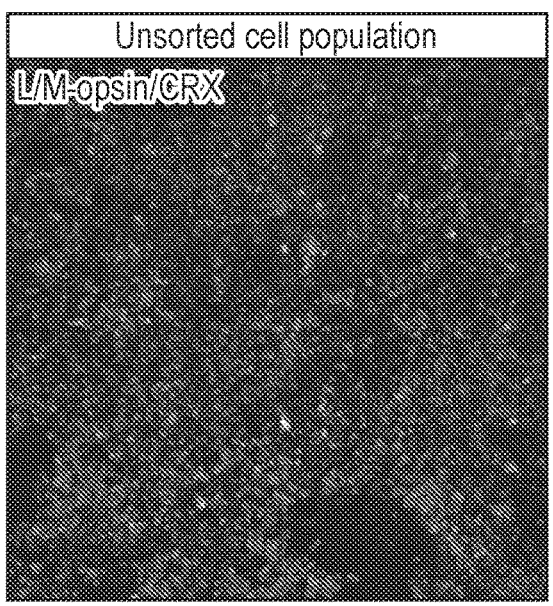
Figure 4D:
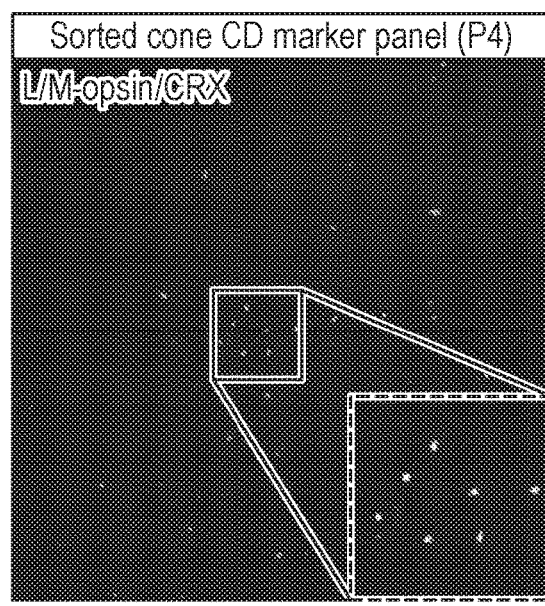
Figure 4E:
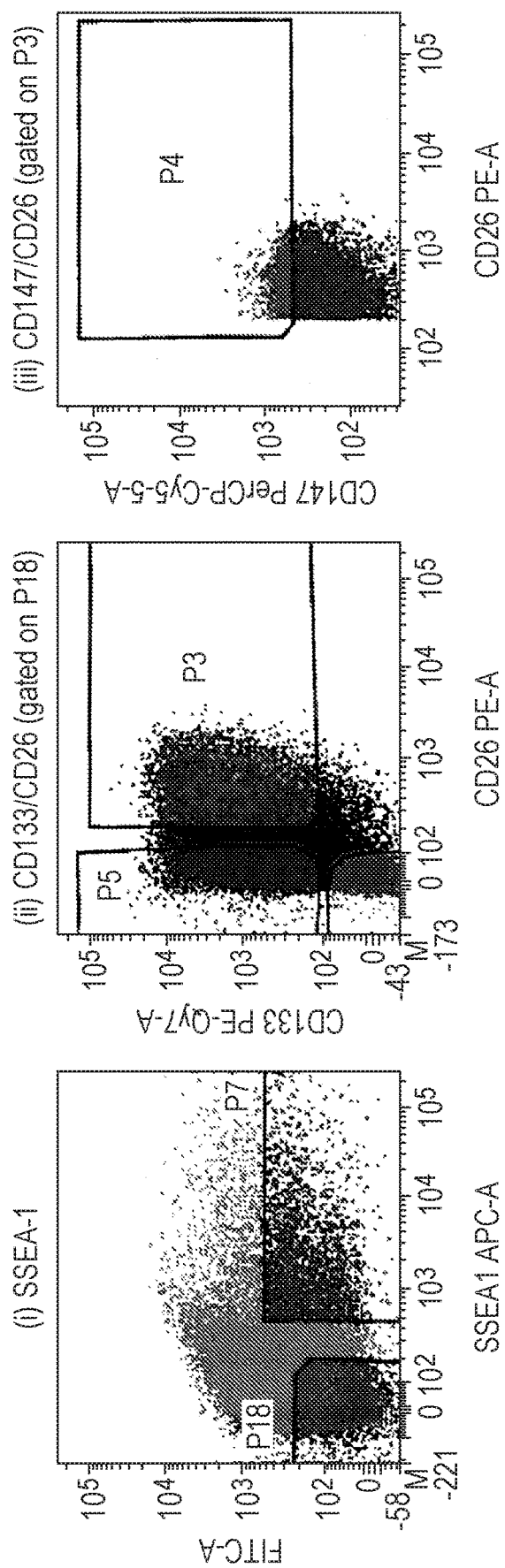
Figure 4F:
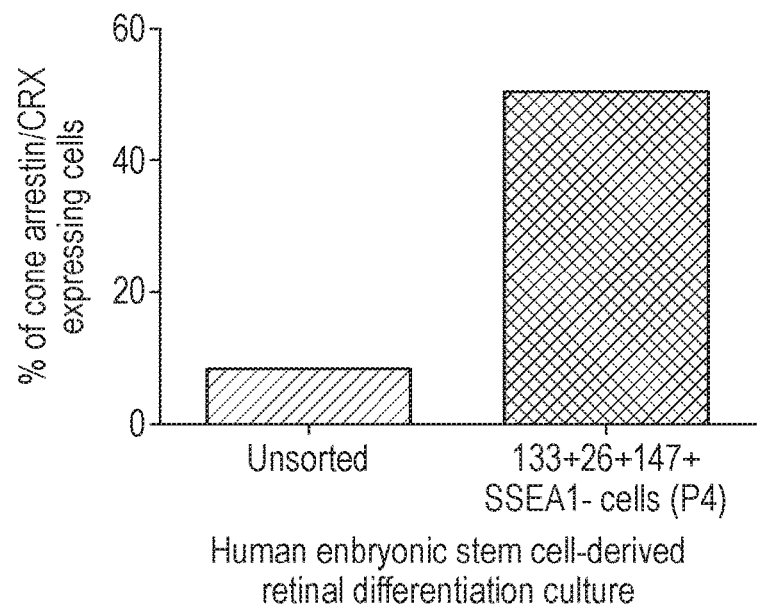
Figure 4G:
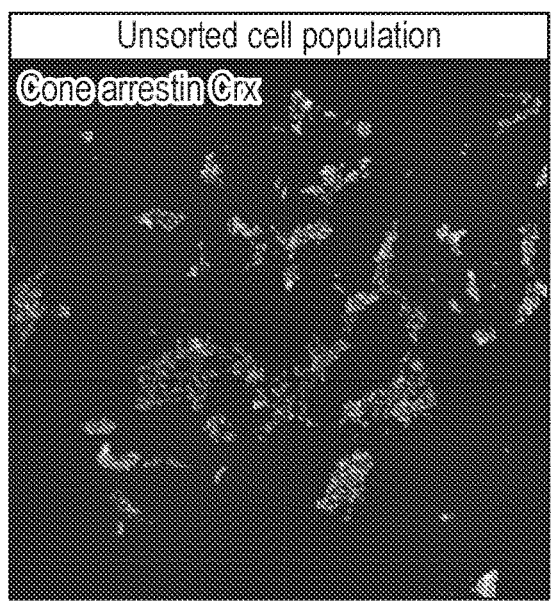
Figure 4H:
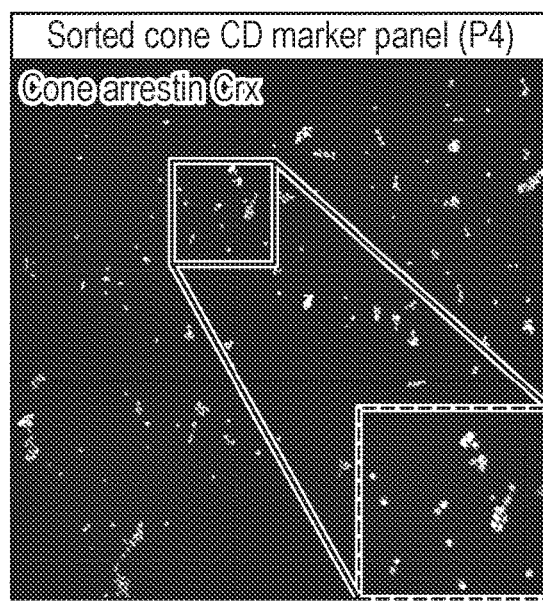

Addition of CD15-SSEA-1 as a negative selection marker in combination with triple positive cone cell selection for human foetal retinal cells (FIG. 4A) (n=3). CD15-SSEA1+ ve cells were first removed from the retinal sample (i) P7; 34.8%±18.5) before sorting with CD26, CD133 and CD147 (i and ii). Using the CD markers in combination within a biomarker panel (FIG. 4A) greatly improved the specificity of LM-opsin and CRX+ cells (30.2%±19.7) within the enriched cell population (CD26+CD133+CD147+SSEA-1−), when compared to the unsorted population (0.14%±0.01; FIG. 4B-D). Additionally, the percentage of LM-opsin/CRX+ cells within the other cell populations, including SSEA-1+, CD133+/CD26+/SSEA1− and CD133−/CD26−/CD147−SSEA1−, was significantly lower compared to the CD26+/CD133+CD147+/SSEA-1− cell population, showing that an enrichment of human L/M-opsin cones can be achieved using this biomarker panel (FIG. 4B). No SSEA-1 labelling of L/M-opsin cones was observed.

Finally the inventors tested the cone biomarker panel on human embryonic stem cell (ESC)-derived retinal differentiation cultures (FIG. 4E-H) to assess if a similar enrichment of cones could be achieved from an in vitro system. The inventors showed that the cone biomarker panel was able to enrich for ARR3 and CRX double positive cells from a starting population of 7% (unsorted) up to 50% in the sorted CD26+/CD133+/CD147+/SSEA1− population (FIG. 4E-H).

The purified population was highly enriched for CRX-expressing cells suggesting the presence of less mature photoreceptors in addition to the cone arrestin-expressing population. The protocol isolated a CD26+CD133+CD147+ SSEA1− population of 22,000 cells from 4 million cells and would require a scale up of 9× in order to achieved 200,000 total cell yield for retinal transplantation (based on studies in the mouse).

CONCLUSIONS

The data show that combinations of positive and negative selector cell surface biomarkers can be used to identify and isolate cone photoreceptors from population of cells. The cone biomarker panel was able to enrich for ARR3 and CRX double positive cells from a starting population of 7% (unsorted) up to 50% when using the preferred biomarker panel CD26+/CD133+/CD147+/SSEA1−.

The CD markers disclosed above are useful in cell enrichment strategies as positive selectors of cones for clinical application. By defining CD markers expressed on human foetal cones the markers can be used to faithfully select iPSC or ESC-derived cones for use in therapy or research.

REFERENCES

EBERLE, D., et al (2011) Increased integration of transplanted CD73-positive photoreceptor precursors into adult mouse retina. *Investigative ophthalmology & visual science* 52(9):6462-6471.

EBERLE, D., et al. (2012) Outer segment formation of transplanted photoreceptor precursor cells. *PloS one* 7(9): e46305.

FEI, Y. & HUGHES, T. E. 2001. Transgenic expression of the jellyfish green fluorescent protein in the cone photoreceptors of the mouse. *Vis Neurosci,* 18, 615-23.

NATHANS, J., DAVENPORT, C. M., MAUMENEE, I. H., LEWIS, R. A., HEJTMANCIK, J. F., LITT, M., LOVRIEN, E., WELEBER, R., BACHYNSKI, B., ZWAS, F. & ET AL. 1989. Molecular genetics of human blue cone monochromacy. *Science,* 245, 831-8.

KOMAROMY, A. M., ALEXANDER, J. J., COOPER, A. E., CHIODO, V. A., GLUSHAKOVA, L. G., ACLAND, G. M., HAUSWIRTH, W. W. & AGUIRRE, G. D. 2008. Targeting gene expression to cones with human cone opsin promoters in recombinant AAV. *Gene Ther,* 15, 1049-55.

LAKOWSKI, J., et al. (2011) Effective transplantation of photoreceptor precursor cells selected via cell surface antigen expression. *Stem cells* 29(9):1391-1404.

LAKOWSKI, J., GONZALEZ-CORDERO, A., WEST, E. L., HAN, Y. T., WELBY, E., NAEEM, A., BLACKFORD, S. J., BAINBRIDGE, J. W., PEARSON, R. A., ALI, R. R. & SOWDEN, J. C. 2015. Transplantation of Photoreceptor Precursors Isolated via a Cell Surface Biomarker Panel From Embryonic Stem Cell-Derived Self-Forming Retina. *Stem Cells,* 33, 2469-82.

LI, Q., TIMMERS, A. M., GUY, J., PANG, J. & HAUSWIRTH, W. W. 2008. Cone-specific expression using a human red opsin promoter in recombinant AAV. *Vision Res,* 48, 332-8.

MERTENS, J., et al 2016. Evaluating cell reprogramming, differentiation and conversion technologies in neuroscience. *Nature Reviews Neuroscience,* 17, 424-437.

MEYER, J. S., SHEARER, R. L., CAPOWSKI, E. E., WRIGHT, L. S., WALLACE, K. A., MCMILLAN, E. L., ZHANG, S. C. & GAMM, D. M. 2009. Modeling early retinal development with human embryonic and induced pluripotent stem cells. *Proc Natl Acad Sci USA,* 106, 16698-703.

WANG, Y., MACKE, J. P., MERBS, S. L., ZACK, D. J., KLAUNBERG, B., BENNETT, J., GEARHART, J. & NATHANS, J. 1992. A locus control region adjacent to the human red and green visual pigment genes. *Neuron,* 9, 429-40.

The invention claimed is:

1. A method of identifying L/M-Opsin and CRX positive cone photoreceptor cells in a population of cells, comprising: a) detecting and determining whether or not cells in the population express CD29 or CD15-SSEA1 on cell surface; b) detecting and determining whether or not cells in the population express at least two of CD26, CD133 and CD 147 on the cell surface; and c) identifying cells as L/M-Opsin and CRX positive cone photoreceptor cells based on presence of L/M-Opsin and CRX, absence of CD29 or CD15-SSEA1, and presence of at least two of CD26, CD133 and CD147, and wherein the cells are L/M-Opsin and CRX positive, CD29 or CD15-SSEA1 negative and positive for at least two of CD26, CD133 and CD147.

2. The method of claim 1, wherein the cells are L/M-Opsin and CRX positive, CD15-SSEA1 negative and positive for at least two of CD26, CD133 and CD147.

3. The method of claim 2, wherein the cells are L/M-Opsin and CRX positive, CD 15-SSEA1 negative and positive for CD26, CD133 and CD147.

4. The method of claim 1, wherein the population of cells are cultured and yielded from: a) human induced pluripotent stem cells or cells derived from human induced pluripotent stem cells; b) human embryonic stem cells or cells derived from human embryonic stem cells; c) human fetal retinal cells or cells derived from human fetal retinal cells; or d) directly converted human somatic cell populations or cells derived from directly converted human somatic cell populations.

5. The method of claim 1, further comprising culturing the population of cells prior to the identification steps, to allow for differentiation of cells to the L/M-Opsin and CRX positive cone photoreceptor populations.

6. The method of claim 1, further comprising a step of isolating the identified L/M-Opsin and CRX positive cone photoreceptor cells from the population of cells by magnetic-activated cell sorting (MACS) or fluorescence-activated cell sorting (FACS).

7. The method of claim 6, further comprising a step of culturing the isolated identified cells to allow the cells to differentiate into mature L/M-Opsin and CRX positive cone photoreceptors.

* * * * *